United States Patent
Dugar et al.

(10) Patent No.: US 6,329,395 B1
(45) Date of Patent: Dec. 11, 2001

(54) NEUROPEPTIDE Y5 RECEPTOR ANTAGONISTS

(75) Inventors: Sundeep Dugar, Bridgewater; Bernard R. Neustadt, West Orange; Andrew W. Stamford, Chatham Township, all of NJ (US); Yusheng Wu, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/326,575

(22) Filed: Jun. 7, 1999

Related U.S. Application Data

(60) Provisional application No. 60/088,422, filed on Jun. 8, 1998.

(51) Int. Cl.[7] .................. A61K 31/445; C07D 211/56
(52) U.S. Cl. .................. 514/329; 514/319; 546/205; 546/224
(58) Field of Search .................. 514/329, 319; 546/224, 205

(56) References Cited

U.S. PATENT DOCUMENTS

| | | | |
|---|---|---|---|
| 4,009,208 | 2/1977 | Lesher | 564/158 |
| 4,184,867 | 1/1980 | Pilgram et al. | 504/334 |
| 4,491,584 | 1/1985 | Banitt | 546/231 |
| 4,623,622 | 11/1986 | De Vries | 435/70.4 |
| 5,378,728 | 1/1995 | Nadelson et al. | 514/507 |

FOREIGN PATENT DOCUMENTS

| | | |
|---|---|---|
| WO 97/20821 | 6/1997 | (WO) . |
| WO 98/35957 | 8/1998 | (WO) . |
| 99/07672 | 2/1999 | (WO) . |

OTHER PUBLICATIONS

Evans, et al, *J. Chem. Soc.*, (1962), pp. 5045–5056.
CA, 113 (1990), p. 693, abstract 113:162464p.
CA, 110 (1989), p. 671, abstract 110:202681y.
CA, 124 (1996), p. 1008, abstract 124:274566b.
CA, 117 (1992), p. 81, abstract 117:9616x.
Huang et al, *J. Med. Chem.*, 41 (1998), pp. 2361–2370.
Baruffini et al. "Phytotoxicity of p–alkylthioanilides" CA 73:86803 (1970).
Ware et al. "3–pyridylmethylaryl ureas" CA 84:59220 (1975).
Forbes et al. :CNS active pyridinylurea derivatives Ca 125:114487 (1996).
Helsley et al. "Synthesis and biological activity . . . " J. Med. Chem. v.11(5) 1034–1037 (1968).

*Primary Examiner*—Ceila Chang
(74) *Attorney, Agent, or Firm*—Anita W. Magatti

(57) ABSTRACT

Compounds of the formula I

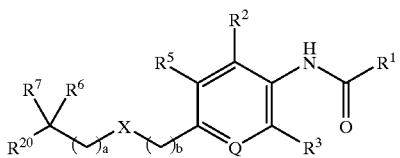

or a pharmaceutically acceptable salt thereof, wherein
a and b are 0–2, provided that the sum is 0–3;

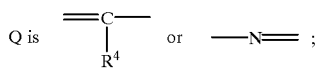

X is —O—, —S—, —SO—, —SO$_2$—, —CH(OR$^8$)—, —C(O)—, —C(R$^{23}$)$_2$—, optionally substituted alkenyl, alkynyl or;

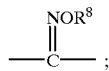

R$^1$ is optionally substituted aryl, heteroaryl, substituted amino, alkyl-OC(O)R$^8$, aryloxyalkyl,

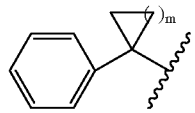

wherein m is 1–4, or

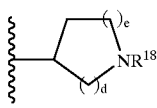

wherein d and e are 0–2;
R$^2$, R$^3$, R$^4$ and R$^5$ are H, alkyl, optionally substituted cycloalkyl, halogen, —OR$^8$, —N(R$^8$)$_2$, —CO$_2$R$^8$ or CF$_3$;
R$^6$ and R$^7$ are H, alkyl, alkenyl, hydroxyalkyl, aminoalkyl, alkoxy-alkyl, cycloalkyl or cycloalkylalkyl, or R$^6$ and R$^7$, form a 3–7-membered carbocyclic ring, or a 4–7-membered heterocyclic ring;
R$^8$ is H, alkyl, cycloalkyl, optionally substituted aryl or heteroaryl;
R$^9$ is alkyl, cycloalkyl, optionally substituted aryl or heteroaryl;
R$^{11}$ is H, alkyl or cycloalkyl; and
R$^{23}$ is R$^8$ or halogen; are claimed, as well as additional novel compounds; also claimed are pharmaceutical compositions and methods of using said novel compounds in the treatment of eating disorders and diabetes.

9 Claims, No Drawings

NEUROPEPTIDE Y5 RECEPTOR ANTAGONISTS

CROSS REFERENCE TO RELATED APPLICATIONS

This application claims the benefit of U.S. Provisional Application 60/088,422, filed Jun. 8, 1998.

BACKGROUND OF THE INVENTION

The present invention relates to selective neuropeptide Y Y5 receptor antagonists useful in the treatment of eating disorders and diabetes, pharmaceutical compositions containing the compounds, and methods of treatment using the compounds.

Neuropeptide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonize neuropeptide Y at the Y5 receptor subtype represent an approach to the treatment of eating disorders such as obesity and hyperphagia.

Phenyl amides and ureas are known as antiatherosclerotic agents, see for example U.S. Pat. No. 4,623,662, and benzoic acid amides are disclosed as antidiabetic agents in U.S. Pat. No. 5,378,728. N,N-alkylenebis-(benzamides) are known as endocrinological agents, see U.S. Pat. No. 4,009,208. WO 98/35957, published Aug. 20, 1998, discloses amide derivatives as selective neuropeptide Y receptor antagonists.

SUMMARY OF THE INVENTION

The present invention relates to compounds represented by the structural formula I

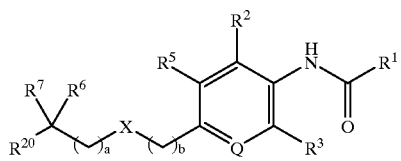

or a pharmaceutically acceptable salt thereof, wherein
a and b are independently 0, 1 or 2, provided that the sum of a and b is 0 to 3;

Q is 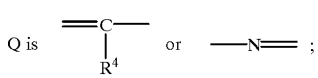 or —N=;

X is —O—, —S—, —SO—, —SO$_2$—, —CH(OR$^8$)—, —C(O)—, —C(R$^{23}$)$_2$—, —C(R$^{25}$)=C(R$^{25}$)—, —C≡C— or

R$^1$ is R$^{15}$-aryl, R$^{24}$-heteroaryl, —NHR$^{12}$, —N(R$^{12}$)$_2$, —(C$_1$–C$_9$)alkyl-OC(O)R$^8$, aryloxy(C$_1$–C$_9$)alkyl,

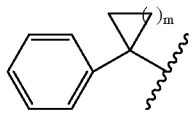

wherein m is 1–4, or

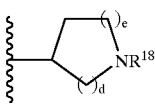

wherein d and e are independently 0, 1 or 2;

R$^2$, R$^3$, R$^4$ and R$^5$ are independently selected from the group consisting of H, C$_1$–C$_5$ straight or branched alkyl, (C$_3$–C$_{12}$)cycloalkyl, R$^{14}$-(C$_3$–C$_{12}$)cycloalkyl, halogen, —OR$^8$, —N(R$^8$)$_2$, —CO$_2$R$^8$ and CF$_3$;

R$^6$ and R$^7$ are independently selected from the group consisting of H, (C$_1$–C$_9$)alkyl, (C$_1$–C$_9$)alkenyl, hydroxy-(C$_1$–C$_9$)alkyl, amino-(C$_1$–C$_9$)-alkyl, (C$_1$–C$_9$) alkoxy-(C$_1$–C$_9$)alkyl, (C$_3$–C$_{12}$)cycloalkyl and (C$_3$–C$_{12}$)-cycloalkyl-(C$_1$–C$_6$)alkyl, or R$^6$ and R$^7$, together with the carbon to which they are attached, form a 3, 4, 5, 6 or 7-membered carbocyclic ring, or a 4, 5, 6 or 7-membered heterocyclic ring, wherein 1, 2 or 3 ring members are independently selected from the group consisting of O, S and N;

R$^8$ is independently selected from the group consisting of H, (C$_1$–C$_6$)alkyl, (C$_3$–C$_{12}$)cycloalkyl, R$^{15}$-aryl and R$^{24}$-heteroaryl;

R$^9$ is (C$_1$–C$_6$)alkyl, (C$_3$–C$_{12}$)cycloalkyl, R$^{15}$-aryl or R$^{24}$-heteroaryl;

R$^{11}$ is independently selected from the group consisting of H, (C$_1$–C$_6$)alkyl and (C$_3$–C$_{12}$)cycloalkyl;

R$^{12}$ is independently selected from the group consisting of straight or branched (C$_1$–C$_9$)alkyl, hydroxy(C$_2$–C$_9$) alkyl, (C$_1$–C$_9$)alkoxy-(C$_2$–C$_9$)-alkyl, N(R$^{11}$)(R$^{19}$)-(C$_2$–C$_9$)-alkyl, HS(C$_2$–C$_9$)-alkyl, (C$_1$–C$_9$)-alkylthio-(C$_2$–C$_9$)-alkyl, (C$_3$–C$_{12}$)-cycloalkyl, R$^{14}$-(C$_3$–C$_{12}$) cycloalkyl, R$^{15}$-aryl, R$^{24}$-heteroaryl, R$^{15}$-aryl(C$_1$–C$_6$)-alkyl, R$^{24}$-heteroaryl(C$_1$–C$_6$)-alkyl,

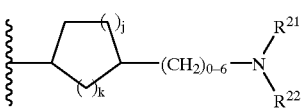

wherein j and k are independently 0, 1 or 2, and

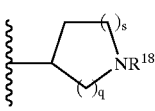

wherein q is 1 or 2, and s is 0, 1 or 2; or two R$^{12}$ groups, together with the nitrogen to which they are attached, form a ring of the formula

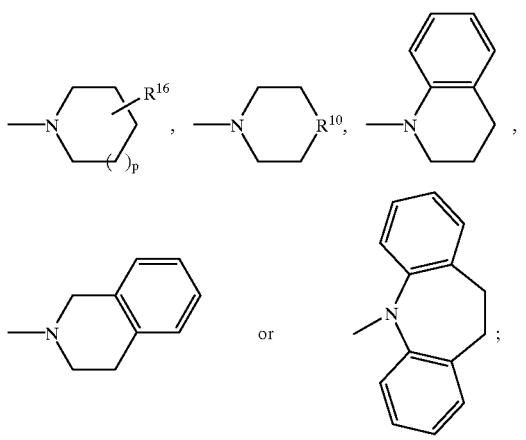

 or wherein p is 0, 1 or 2;
R$^{10}$ is —NR$^{18}$—, —O— or —S—;
R$^{13}$ is 1 to 3 substituents independently selected from the group consisting of hydrogen, (C$_1$–C$_6$)alkyl, halogen, (C$_1$–C$_6$)alkoxy and CF$_3$;
R$^{14}$ is 1 to 3 substituents independently selected from the group consisting of (C$_1$–C$_6$)alkyl, benzyl, R$^{13}$-aryl and R$^{13}$-heteroaryl;
R$^{15}$ is 1 to 3 substituents independently selected from the group consisting of hydrogen, (C$_1$–C$_6$)alkyl, halo, polyhalo(C$_1$–C$_6$)alkyl, R$^{17}$O—, —N(R$^{17}$)$_2$, —S(R$^{17}$), R$^{17}$O—(C$_1$–C$_6$)alkyl, (R$^{17}$)$_2$N—(C$_1$–C$_6$)alkyl formyl, —C(O)R$^{17}$, —COOR$^{17}$, —CON(R$^{17}$)$_2$, —OC(O)N(R$^{17}$)$_2$, —N(R$^{17}$)C(O)N(R$^{17}$)$_2$, —NR$^{17}$C(O)R$^{17}$, —NR$^{17}$C(O)OR$^{14}$, R$^{17}$S(O)—, R$^{17}$SO$_2$—, R$^{17}$SO$_2$NR$^{17}$— and tri(C$_1$–C$_6$)-alkylsilyl;
R$^{16}$ is 1–3 substituents independently selected from the group consisting of H, (C$_1$–C$_6$)alkyl, (C$_3$–C$_{12}$)cycloalkyl, (C$_3$–C$_{12}$)spirocycloalkyl, (C$_3$–C$_4$)spiroalkylenedioxy, R$^{15}$-aryl, R$^{24}$-heteroaryl, benzyl, N-piperidinyl, —COR$^8$, —C(O)NR$^8$R$^9$, —NR$^8$R$^9$ and —NR$^8$C(O)R$^9$, or when two R$^{16}$ groups are attached to adjacent ring carbon atoms, together with said carbon atoms, they can form a (C$_5$–C$_7$) cycloalkyl ring;
R$^{17}$ is independently selected from the group consisting of H, (C$_1$–C$_6$)alkyl, (C$_3$–C$_{12}$)cycloalkyl, (C$_3$–C$_{12}$)cycloalkyl(C$_1$–C$_6$)alkyl, R$^{13}$-aryl and R$^{13}$-heteroaryl;
R$^{18}$ is independently selected from the group consisting of H, (C$_1$–C$_6$)alkyl, (C$_3$–C$_{12}$)cycloalkyl, (C$_3$–C$_{12}$)cycloalkyl-(C$_1$–C$_6$)alkyl, R$^{15}$-aryl, R$^{24}$-heteroaryl, —CO$_2$R$^9$, —C(O)N(R$^8$)$_2$, —COR$^8$ and —SO$_2$R$^9$;
R$^{19}$ is H, (C$_3$–C$_{12}$)cycloalkyl-(C$_1$–C$_6$)alkyl, R$^{15}$-aryl, R$^{24}$-heteroaryl, —CO$_2$R$^9$, —C(O)N(R$^8$)$_2$, —COR$^8$ or —SO$_2$R$^9$;
R$^{20}$ is (C$_1$–C$_6$)alkyl, (C$_3$–C$_{12}$)cycloalkyl, (C$_3$–C$_{12}$)cycloalkyl-(C$_1$–C$_6$)alkyl, hydroxy(C$_1$–C$_6$)alkyl, oxo (C$_1$–C$_6$)alkyl or polyhalo(C$_1$–C$_6$)alkyl;
R$^{21}$ and R$^{22}$ are independently selected from the group consisting of H, (C$_1$–C$_6$)alkyl, (C$_3$–C$_{12}$)cycloalkyl-(C$_1$–C$_6$)alkyl, hydroxy(C$_1$–C$_6$)alkyl, R$^{15}$-aryl, R$^{24}$-heteroaryl, R$^{15}$-aryl(C$_1$–C$_6$)alkyl or R$^{24}$-heteroaryl (C$_1$–C$_6$)-alkyl;
R$^{23}$ is independently selected from the group consisting of H, halogen, (C$_1$–C$_6$)alkyl, (C$_3$–C$_{12}$)cycloalkyl, R$^{15}$-aryl, and R$^{24}$-heteroaryl;
R$^{24}$ is 1 to 2 substituents independently selected from the group consisting of hydrogen, (C$_1$–C$_6$)alkyl, halo, polyhalo(C$_1$–C$_6$)alkyl, R$^{17}$O—, —N(R$^{17}$)$_2$, —S(R$^{17}$), R$^{17}$O—(C$_1$–C$_6$)alkyl, (R$^{17}$)$_2$N—(C$_1$–C$_6$) alkyl, formyl, —C(O)R$^{17}$, —COOR$^{17}$, —CON(R$^{17}$)$_2$, —OC(O)N(R$^{17}$)$_2$, —N(R$^{17}$)C(O)N(R$^{17}$)$_2$, —NR$^{17}$C(O)R$^{17}$, —NR$^{17}$C(O)OR$^{14}$, R$^{17}$S(O)—, R$^{17}$SO$_2$—, R$^{17}$SO$_2$NR$^{17}$— and tri(C$_1$–C$_6$)-alkylsilyl; and
R$^{25}$ is independently selected from the group consisting of hydrogen, halogen, (C$_1$–C$_6$)-alkyl and polyhalo (C$_1$–C$_6$)alkyl.

In a preferred group of compounds of formula I, Q is $$=\!\!\underset{R^4}{\overset{|}{C}}\!\!-$$

wherein R$^4$ is H. Also preferred are compounds wherein R$^3$ is H, and wherein R$^2$ and R$^5$ are independently H or halogen. R$^6$ and R$^7$ are preferably (C$_1$–C$_9$)alkyl, especially methyl, or R$^6$ and R$^7$, together with the carbon to which they are attached, form a C$_3$–C$_6$ carbocyclic ring.

In compounds of formula I, X is preferably —S—; —C(O)—; or —C(R$^8$)$_2$, especially wherein R$^8$ is H. More preferably, X is —C(R$^8$)$_2$—, and compounds wherein X is —CH$_2$— are especially preferred.

In compounds of formula I, a is preferably 1 or 2 and b is preferably 0.

In compounds of formula I, R$^1$ is preferably —NHR$^{12}$ or —N(R$^{12}$)$_2$, especially

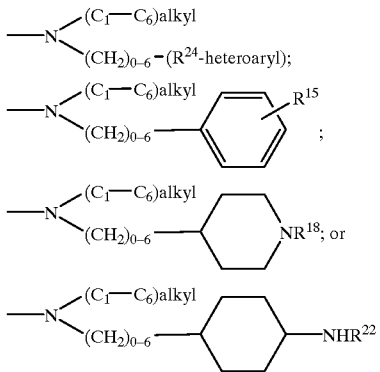

wherein R$^{18}$ is (C$_1$–C$_6$)alkyl or —SO$_2$R$^9$; R$^9$ is (C$_1$–C$_6$) alkyl or aryl; and R$^{22}$ is (C$_1$–C$_6$)alkyl or (C$_3$–C$_{12}$)cycloalkyl (C$_1$–C$_6$)alkyl.

Another aspect of the invention is a pharmaceutical composition for treating eating disorders or diabetes which comprises an effective amount of a compound of formula I in combination with a pharmaceutically acceptable carrier.

Yet another aspect of this invention is a method of treating an eating disorder or diabetes comprising administering an effective amount of a compound of formula I to a patient in need of such treatment.

Also claimed are novel compounds similar to those of formula I wherein b is 0, X is —O— or —S—and the substituent corresponding to R$^1$ is optionally substituted alkyl.

DETAILED DESCRIPTION

Except where stated otherwise the following definitions apply throughout the present specification and claims. These definitions apply regardless of whether a term is used by itself or in combination with other terms. Hence the definition of "alkyl" applies to "alkyl" as well as the "alkyl" portions of "alkoxy", etc.

Alkyl represents a straight or branched saturated hydrocarbon chains having the designated number of carbon atoms. If the number of carbon atoms is not specified, e.g., if the term lower alkyl is used, chain lengths of 1 to 6 carbons are intended.

When X is $-C(R^{25})=C(R^{25})-$, both cis and trans configurations are comtemplated.

Cycloalkyl represents a saturated carbocyclic ring having 3 to 12 carbon atoms. Preferred are $C_3-C_6$cycloalkyl rings.

In the definition of $R^{16}$, the term $(C_3-C_{12})$spirocycloalkyl refers to a $(C_2-C_{11})$alkylene chain joined at both ends to the same ring carbon, i.e.,

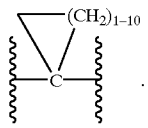

Similarly, the term $(C_3-C_4)$spiroalkylenedioxy refers to a $(C_2-C_3)$alkylenedioxy group joined at both ends to the same ring carbon atom, i.e.,

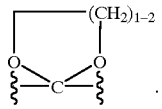

In the definition of $R^6$ and $R^7$, the term "heterocyclic ring" refers to 4- to 7-membered saturated rings comprising 1 to 3 heteroatoms independently selected from the group consisting of $-O-$, $-S-$ and $-NH-$, with the remaining ring members being carbon. Where a heterocyclic ring comprises more than one heteroatom, no rings are formed where there are adjacent oxygen atoms, adjacent sulfur atoms, or three consecutive heteroatoms. Examples of heterocyclic rings are tetrahydrofuranyl, pyrrolidinyl, piperidinyl, morpholinyl, thiomorpholinyl and piperazinyl.

When two $R^{12}$ groups form a ring of the formula

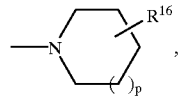

those skilled in the art will recognize that $-NR^8R^9$ and $-NR^8C(O)R^9$ substituents cannot be attached to a carbon adjacent to the piperizinyl nitrogen.

Halogen represents fluoro, chloro, bromo or iodo.

Polyhalo($C_1-C_6$)alkyl refers to a straight or branched alkyl chain substituted by 1 to 5 halogen atoms, which can be attached to the same or different carbon atoms, e.g., $-CH_2F$, $-CHF_2$, $-CF_3$, $F_3CCH_2-$ and $-CF_2CF_3$.

Hydroxy($C_1-C_6$)alkyl refers to an alkyl chain substituted on any substitutable carbon by a hydroxy group. Similarly, oxo($C_1-C_6$)alkyl refers to an alkyl chain substituted by an $=O$ moiety.

Aryl represents phenyl or naphthyl.

Heteroaryl refers to 5- to 10-membered single or benzofused aromatic rings comprising 1 to 3 heteroatoms independently selected from the group consisting of $-O-$, $-S-$ and $-N=$, provided that the rings do not include adjacent oxygen and/or sulfur atoms. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are quinolinyl, isoquinolinyl, quinazolinyl, thianaphthenyl (i.e., benzothienyl), indolyl, benzimidazolyl, benzofuranyl and benzofurazanyl. N-oxides of nitrogen-containing heteroaryl groups are also included. All positional isomers are contemplated, e.g., 2-pyridyl, 3-pyridyl and 4-pyridyl. Preferred heteroaryl groups are pyridyl, isoxazolyl, thienyl, thiazolyl, pyrazinyl, pyrimidinyl, pyridazinyl, quinolinyl, isoquinolinyl and quinazolinyl.

When a variable appears more than once in the structural formula, for example $R^8$, the identity of each variable appearing more than once may be independently selected from the definition for that variable.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Compounds of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I may be produced by processes known to those skilled in the art as shown in the examples below. Typically, the claimed compounds wherein X is $-S-$ or $-O-$ can be prepared as shown in the following reaction scheme:

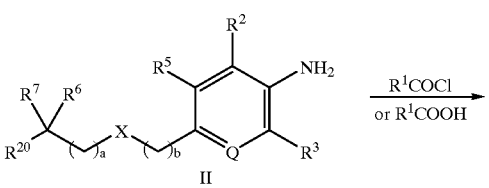

II

-continued

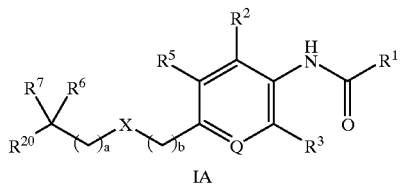

IA wherein an amine of formula II is reacted with an acid chloride or carbamoyl chloride in the presence of a base, or with a carboxylic acid in the presence of standard amide coupling agents such as EDC and DMAP. Starting materials of formula II can be prepared using known methods.

The compounds of formula I exhibit selective neuropeptide Y5 antagonizing activity, which has been correlated with pharmacological activity for treating eating disorders such as obesity and hyperphagia.

The compounds of formula I display pharmacological activity in test procedures designated to indicate neuropeptide Y5 receptor antagonist activity. The compounds are non-toxic at pharmaceutically therapeutic doses. Following are descriptions of the test procedures.

cAMP Assay

CHO cells expressing the various NPY receptor subtypes were maintained in Ham's F-12 media (Gibco-BRL) supplemented with 10% FCS (ICN), 1% penicillin-streptomycin, 1% non-essential amino acids and 200 µg/ml Geneticin® (GibcoBRL #11811-031) under a humidified 5% $CO_2$ atmosphere. Similarly, HEK-293 cells expressing the various NPY receptor subtypes were maintained in Dulbecco's modified Eagle's media (Gibco-BRL.) supplemented with 10% FCS (ICN), 1% penicillin-streptomycin and 200 µg/ml Geneticin® (GibcoBRL #11811-031) under a humidified 5% $CO_2$ atmosphere. Two days prior to assay, cells were released from T-175 tissue culture flasks using cell dissociation solution (1X; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then preincubated with approximately 150 µl/well of assay buffer (HBSS supplemented with 4 mM $MgCl_2$, 10 mM HEPES, 0.2% BSA [HH]) containing 1 mM 3-isobutyl-1-methylxanthine ([IBMX] Sigma #I-5879) with or without the antagonist compound of interest at 37° C. After 20 minutes the 1 mM IBMX-HH assay buffer (± antagonist compound) was removed and replaced with assay buffer containing 1.5 µM (CHO cells) or 5 µM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 µl ethanol. The tissue culture plates were agitated on a platform shaker for 15 minutes, after which the plates were transferred to a warm water bath in order to evaporate the ethanol. Upon bringing all wells to dryness, the cell residues were resolubilized with 250 µl FlashPlate® assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control. All data points were determined in triplicate and $EC_{50}$'s (nM) were calculated using a nonlinear (sigmoidal) regression equation (GraphPad Prism™). The $K_B$ of the antagonist compound was estimated using the following formula:

$K_B=[B]/(1-\{[A']/[A]\})$ where [A] is the $EC_{50}$ of the agonist (NPY) in the absence of antagonist,

[A'] is the $EC_{50}$ of the agonist (NPY) in the presence of antagonist, and

[B] is the concentration of the antagonist.

NPY Receptor Binding Assay

Human NPY receptors were expressed in CHO cells. Binding assays were performed in 50 mM HEPES, pH. 7.2, 2.5 mM $CaCl_2$, 1 mM $MgCl_2$ and 0.1% BSA containing 5–10 ug of membrane protein and 0.1 nM $^{125}$I-peptide YY (for NPY1, NPY2 and NPY5 receptors) or 0.1 nM $^{125}$I-pancreatic polypeptide (NPY4 receptor) in a total volume of 200 ul. Non-specific binding was determined in the presence of 1 uM NPY. The reaction mixtures were incubated for 90 minutes at 30° C. (NPY1 receptor) or at room temperature (NPY2, NPY4 and NPY5 receptors), then filtered through Millipore MAFC glass fiber filter plates which had been pre-soaked in 0.5% polyethyleneimine. The filters were washed with phosphate-buffered saline, and radioactivity was measured in a Packard TopCount scintillation counter.

For the compounds of this invention, a range of neuropeptide Y5 receptor binding activity from about 0.1 to about 1000 nM was observed. Compounds of this invention preferably have a binding activity in the range of about 0.1 to 250 nM, more preferably about 0.1 to 100 nM, and most preferably about 0.1 to 10 nM.

Neuropeptide Y5 receptor binding activity results for representative compounds of the invention are as follows:

| Ex. | r/h Y5 Ki nM |
| --- | --- |
| 1 | 3 |
| 1M | 152 |
| 2X | 50 |
| 2Al | 697 |
| 3 | 9 |
| 6 | 13 |
| 6C | 668 |
| 6N | 66 |
| 8D | 18 |
| 13A | 0.8 |
| 19 | 0.4 |

For preparing pharmaceutical compositions from the compounds of formula I, pharmaceutically acceptable, inert carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as dilutents, flavoring agents, solubilizers, lubricants, suspending agents, binders or tablet disintegrating agents; it may also be an encapsulating material.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parentertal administration. Such liquid forms include solutions, suspensions and emulsions. These particular solid form preparations are most conveniently provided in unit dose form and as such are used to provide a single liquid dosage unit.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from about 0.5 mg to 500 mg, preferably about 0.5 to 100 mg, according to the particular application and the potency of the active ingredient and the intended treatment. The composition may, if desired, also contain other therapeutic agents.

The daily dosage is about 0.01 to about 20 mg/kg. The dosage may be varied depending on the requirement of the patient, the severity of the condition being treated and the particular compound being employed. Determination of the proper dosage for a particular situation is within the skill of those in the medical art. For convenience, the total daily dosage may be divided and administered in portions throughout the day or by means providing continuous delivery.

The invention disclosed herein is exemplified by the following examples which should not be construed to limit the scope of the disclosure. Alternative mechanistic pathways and analogous structures may be apparent to those skilled in the art.

In the examples, the following abbreviations are used: phenyl (Ph), acetyl (Ac), ether ($Et_2O$), ethyl acetate (EtOAc), dimethylformamide (DMF) and ethanol (EtOH). Room temperature is RT.

Preparation 1

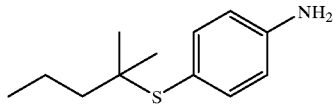

1

To a stirred mixture of 4-aminothiophenol (12.52 g, 0.100 mol) and 2-methyl-1-pentene (25.30 g, 0.300 mol) in anhydrous $Et_2O$ (100 ml) was added concentrated $H_2SO_4$ (15.3 ml, 0.300 mol) cautiously. The clear solution was stirred for 45 min, then poured into cold sat'd $NaHCO_3$ (200 ml). The resultant white solid was collected, washed with cold water several times and dried in vacuo to afford 1 (100%). $^1$H NMR (400 MHz, $CDCl_3$) δ 7.33 (d, 2H, J=8.7 Hz, ArH), 6.68 (d, 2H, J=8.6 Hz, ArH), 1.47 (m, 4H, $CH_2CH_2CH_3$), 1.24 (s, 9H, $(CH_3)_3C$), 0.97 (t, 3H, J=7.0 Hz, $CH_2CH_3$).

Preparation 2

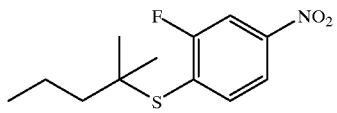

2

A mixture of 3,4-difluoronitrobenzene (1.0 ml, 9.03 mmol) and $Na_2S \cdot 9H_2O$ (3.25 g, 13.5 mmol) in DMF (10 ml) was stirred at RT for 20 h, then poured into cold water. The whole was extracted with $CH_2Cl_2$ (3×100 ml). The combined organic layers were dried ($Na_2SO_4$), filtered and concentrated. To the residue was added 2-methyl-1-pentene (2.2 ml, 18.1 mmol) and $Et_2O$ (5.0 ml). To the vigorously stirred mixture was slowly added concentrated $H_2SO_4$ (1.0 ml). After 1 h the reaction mixture was poured into cold water. The whole was extracted with $CH_2Cl_2$ (3×100 ml), and the combined organic layers were dried ($Na_2SO_4$), filtered and evaporated. Purification of the residue by flash column chromatography (1:20 EtOAc/hexanes) afforded 2 (100%). $^1$H NMR ($CDCl_3$, 400 MHz) δ 8.07 (m, 2H, ArH), 7.34 (t, 1H, ArH), 1.59 (m, 4H, $CH_3CH_2CH_2$), 1.37 (s, 6H, $C(CH_3)_2S$), 1.01 (m, 3H, $CH_3CH_2CH_2$).

Preparation 3

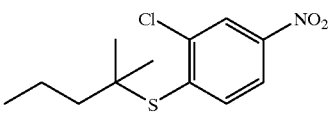

3

A mixture of S-(1,1-dimethylbutyl)thiouronium 4-toluene-sulfonate (prepared as described: Evans, M. B.et al., J. Chem. Soc., (1962), p. 5045) (5.00 g, 15.0 mmol), KOH (2.10 g, 37.5 mmol) and concentrated $NH_3$ (1 drop) in EtOH (20 ml) was refluxed for 1 h. To the reaction mixture was added 3-chloro-4-fluoronitrobenzene in EtOH (10 ml). The mixture was refluxed for 0.5 h, allowed to cool and poured into cold water. The whole was extracted with $CH_2Cl_2$ (3×100 ml). The combined organic layers were dried ($Na_2SO_4$), filtered and concentrated to afford 3 (84%) which was used without further purification. $^1$H NMR ($CDCl_3$, 400 MHz) δ 8.35 (d, 1H, J=2.4 Hz, ArH), 8.09 (dd, 1H, J=2.4, 8.5 Hz, ArH), 7.78 (d, 1H, J=8.5 Hz, ArH), 1.62 (m, 4H, $CH_3CH_2CH_2$), 1.40 (s, 6H, $C(CH_3)_2S$), 0.98 (m, 3H, $CH_3CH_2CH_2$).

Preparation 4

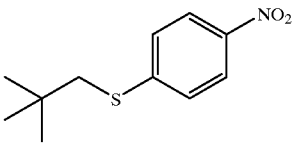

4

A mixture of 4-nitrothiophenol (500 mg, 3.22 mmol), 1-iodo-2,2-dimethylpropane (0.43 ml, 4.8 mmol), and NaH (80%, 97 mg, 3.2 mmol) in DMF (10 ml) was stirred for 3 days. The reaction mixture was poured into $H_2O$ and the whole was extracted with $CH_2Cl_2$. The combined organic layers were dried ($Na_2SO_4$), filtered and evaporated. The residue was subjected to flash chromatography (1:50 EtOAc/hexanes) to afford 4 (190 mg, 26%) as a solid. $^1$H NMR ($CDCl_3$, 400 MHz) δ 8.07 (m, 2H, ArH), 7.31 (m, 2H, ArH), 2.93 (s, 2H, $CH_2S$), 1.05 (s, 9H, $(CH_3)_3$).

Preparation 5

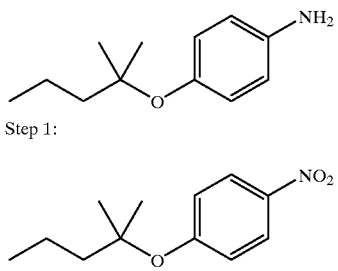

Step 1:

To an ice-cold solution of 2-methyl-2-pentanol (1.5 ml, 15 mmol) in DMF (20 ml) was added NaH (60% dispersion in mineral oil, 600 mg, 15 mmol) under a $N_2$ atmosphere. The cold bath was removed and the suspension was stirred for 4 h. The mixture was cooled in an ice bath, 4-fluoronitrobenzene (1.1 ml, 10 mmol) was added in one portion, and the reaction mixture was stirred at RT. After 18 h, the reaction mixture was poured onto an ice-water slurry (300 ml) and extracted with $Et_2O$ (3×200 ml). The combined $Et_2O$ extracts were washed with $H_2O$ (6×200 ml) and saturated NaCl, dried ($MgSO_4$), filtered and evaporated to afford an oil (2.4 g). Flash chromatography (3:1 hexanes/$CH_2Cl_2$) of the crude product gave 6 (1.50 g, 67%) as an oil. $^1$H NMR ($CDCl_3$, 400 MHz) δ 8.22 (2H, m, ArH), 7.09 (2H, m, ArH), 1.77 (2H, m, —OC($CH_3$)$_2$$CH_2$—), 1.52 (2H, m, —$CH_2$$CH_3$), 1.47 (6H, s, —OC($CH_3$)$_2$—), 1.03 (3H, t, J=7.3 Hz, —$CH_2$$CH_3$). MS (CI) m/e 224 (M+H)$^+$.

Step 2: A mixture of 6 (1.40 g, 6.3 mmol) and 10% Pd/C (0.14 g) in $CH_3OH$ (40 ml) was stirred under a balloon of $H_2$. After 16 h, the catalyst was removed by filtration through celite, and the filter pad was washed with $CH_3OH$. The combined filtrate and washings were evaporated to afford 5 as an oil (1.21 g, 100%). $^1$H NMR ($CDCl_3$, 400 MHz) δ 6.83 (2H, m, ArH), 6.66 (2H, m, ArH), 1.61–1.50 (4H, m, —$CH_2CH_2$—), 1.25 (6H, s, —OC($CH_3$)$_2$—), 0.98 (3H, t, J=7.1Hz, —$CH_2$$CH_3$).

Preparation 6

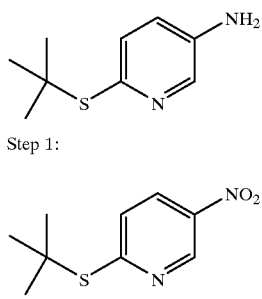

Step 1:

To a solution of 2-chloro-5-nitropyridine (1.00 g, 6.3 mmol) in EtOH (10 ml) was added a solution of potassium 2-mnethyl-2-propanethiolate prepared from 2-methyl-2-propanethiol (0.71 ml, 6.3 mmol) and KOH (0.56 g, 10 mmol) in EtOH (10 ml). The reaction mixture was refluxed for 0.25 h, then cooled in ice. The solid was removed by filtration through celite and the filtrate was evaporated to a syrup, which was dissolved in $CH_2Cl_2$ (100 ml) and washed with sat'd $NH_4Cl$. The organic layer was dried ($MgSO_4$), filtered, and evaporated. Purification of the residue by flash chromatography (1:4 $CH_2Cl_2$/hexanes) gave 8 (0.80 g, 60%) as a waxy solid. $^1$H NMR ($CDCl_3$, 400 MHz) δ 9.31 (1H, d, J=2.8 Hz, ArH), 8.23 (1H, dd, J=8.9, 2.8 Hz, ArH), 7.28 (1H, d, J=8.9 Hz, ArH), 1.70 (9H, s, —S($CH_3$)$_3$).

Step 2: To a solution of 8 (414 mg, 1.95 mmol) and $NiCl_2.6H_2O$ (950 mg, 4.0 mmol) in $CH_3OH$ (20 ml) was added $NaBH_4$ (301 mg, 8.0 mmol) in small portions. After 20 min. the reaction mixture was concentrated and the residue was purified by flash chromatography (3:97 $CH_3OH$/$CH_2Cl_2$) to give 7 (120 mg, 34%). $^1$H NMR ($CDCl_3$, 400 MHz) δ 8.35 (1H, d, J=2.4 Hz, ArH), 7.43 (1H, d, J=8.3 Hz, ArH), 7.30 (1H, dd, J=8.3, 2.4 Hz, ArH), 6.9 (2H, bs, $NH_2$), 1.43 (9H, s, —S($CH_3$)$_3$).

Preparation 7

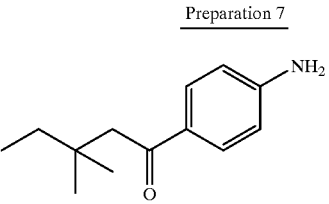

Step 1: A mixture of 3,3-dimethylpentanoic acid (11.00 g, 84.0 mmol; Synthesis (1985), 493) and $SOCl_2$ (80.0 g, 678 mmol) was refluxed for 2 h. The reaction mixture was concentrated in vacuo to afford the acid chloride as a colorless oil (10.0 g, 80%). $^1$H NMR ($CDCl_3$, 400 MHz) δ 2.83 (2H, s, $CH_2$CO), 1.39 (2H, q, J=7.3 Hz, $CH_3$$CH_2$), 1.02 (6H, s, C($CH_3$)$_2$), 0.86 (3H, t, J=7.3 Hz, $CH_3$$CH_2$).

Step 2:

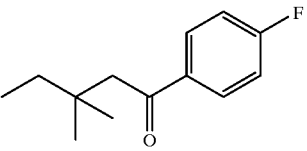

To an ice-cold solution of the product of Step 1 (6.00 g, 41.0 mmol) in dry $Et_2O$ (40 ml) was slowly added 1.0 M 4-fluorophenylmagnesium bromide in THF (37 ml, 37 mmol). The reaction mixture was stirred at 0° C. for 3 h, then poured into 1 N HCl solution (100 ml). The whole was extracted with EtOAc (3×100 ml) and the combined organic layers were dried ($Na_2SO_4$), filtered and evaporated. Purification of the residue by flash chromatography (hexane) afforded the product (7.00 g, 82%) as colorless oil. $^1$H NMR ($CDCl_3$, 400 MHz) δ 7.90 (2H, m, ArH), 7.05 (2H,m, ArH), 2.80 (2H, s, $CH_2$CO), 1.4 (2H, q, J=8.0 Hz, $CH_3$$CH_2$), 0.87 (6H, s, ($CH_3$)$_2$C), 0.85 (3H, t, J=7.6 Hz, $CH_3$$CH_2$). MS (ES) m/e 209 (M+H)$^+$.

Step 3: To a solution of the product of Step 2 (2.00 g, 9.60 mmol) in DMSO (20.0 ml) in a sealed tube was added $NaN_3$ (6.24 g, 96.0 mmol). The vigorously stirred reaction mixture was heated at 140° C. for 5 days, then allowed to cool to RT and poured into 1N NaOH (100 ml). The whole was extracted with EtOAc (3×100 ml). The combined organic layers were dried ($Na_2SO_4$), filtered, and concentrated. Flash chromatography of the residue (1:4 EtOAc/hexane) afforded Preparation 7 (0.66g, 33%) as a light brown oil. $^1$H NMR ($CDCl_3$, 400 MHz) δ 7.80 (2H, d, J=8.8 Hz, ArH), 6.70 (2H, d, J=8.8 Hz, ArH), 2.74 (2H, s, $CH_2$CO), 1.40 (2H, q, J=7.6 Hz, $CH_2$$CH_3$), 0.98 (6H, s, ($CH_3$)$_2$C), 0.86 (3H, t, J=7.6 Hz, $CH_3$$CH_2$). MS (FAB) m/e 206 (M+H)$^+$.

Preparation 8

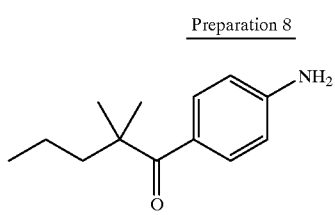

Using 2,2-dimethylpentanoic acid as the starting material and the three-step procedure described for Preparation 7, the title compound was prepared: $^1$H NMR (CDCl$_3$, 400 MHz) δ 7.76 (2H, m), 6.61 (2H, m), 4.05 (2H, bs), 1.76 (2H, m), 1.30 (6H, s), 1.20 (4H, m), 0.83 (3H, t, J=7.8 Hz). MS m/e 206 (M+H)$^+$.

Preparation 9

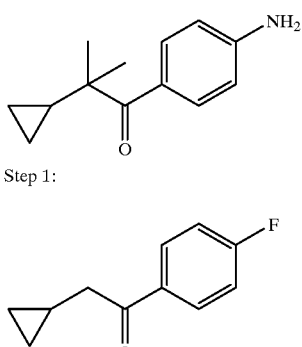

Step 1:

To an ice-cold solution of cyclopropylacetonitrile (4.7 g, 58 mmol) in anhydrous Et$_2$O (30ml) was added 2M 4-fluorophenylmagnesium bromide in Et$_2$O (25 ml, 50 mmol), and the reaction mixture was stirred at 0° C. for 2 h. The reaction mixture was allowed to warm to RT and stirred for an additional 2 h. The pH was adjusted to 3 by addition of 1N HCl and the whole was extracted with Et$_2$O (4×50 ml). The combined Et$_2$O layers were washed with saturated Na$_2$CO$_3$ and NaCl, dried (MgSO$_4$), filtered and concentrated. Flash chromatography (2:98 EtOAc/hexane) of the residue afforded the product (5.02 g, 56%). $^1$H NMR (CDCl$_3$, 400 MHz) δ 7.98(2H, m), 7.13 (2H, t), 2.85 (2H, d), 1.15 (1H, m), 0.61 (2H, m), 0.19 (2H, m). MS m/e 179 (M+H)$^+$.

Step 2:

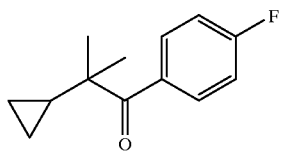

To a stirred, ice-cold solution of the product of Step 1 (5.0 g, 28 mmol) in anhydrous THF (100 ml) under N$_2$ was added KH (16.0 g, 35% in mineral oil, 140 mmol), and the reaction mixture was stirred for 0.5 h. Then CH$_3$I (16 ml, 280 mmol) was added dropwise to the ice-cold reaction mixture. After stirring at RT for 4 h, the reaction mixture was cooled in an ice-bath and sat'd NH$_4$Cl was cautiously added. The whole was extracted with EtOAc (3×100 ml), washed with H$_2$O and sat'd NaCl, dried (MgSO$_4$), filtered, and concentrated. Flash chromatography (hexanes, then 1:9 EtOAc/hexanes) afforded the product (3.96 g, 68%). $^1$H NMR (CDCl$_3$, 400 MHz) δ 7.84 (2H, m), 7.07 (2H, m), 1.14 (6H, s), 1.13 (1H, m), 0.51 (2H, m), 0.42 (2H, m).

Step 3: Using the procedure of Preparation 7, Step 3, reaction of the product of Step 2 with NaN$_3$ afforded Preparation 9. $^1$H NMR (CDCl$_3$, 400 MHz) δ 7.86 (2H, m), 6.67 (2H, m), 4.42 (2H, bs), 1.16 (1H, m), 1.15 (6H, s), 0.49 (2H, m), 0.42 (2H, m).

Preparation 10

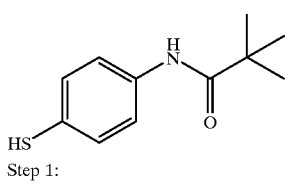

Step 1:

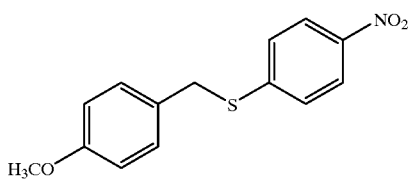

A mixture of 4-fluoronitrobenzene (10.0 g, 70.9 mmol), 4-methoxybenzylmercaptan (14.8 mL, 106 mmol), and K$_2$CO$_3$ (19.6 g, 142 mmol) in acetone (150 mL) was refluxed for 4 h. The cooled reaction mixture was poured into H$_2$O and extracted with CH$_2$Cl$_2$ (3×100 mL). The combined organic extracts were dried (Na$_2$SO$_4$), filtered, and concentrated to afford an oil (17.1 g, 87%) that was used without further purification. $^1$H NMR (CDCl$_3$, 400 MHz) δ 8.18 (m, 2H, ArH), 7.38 (m, 4H, ArH), 6.94 (m, 2H, ArH), 4.28 (s, 2H, —CH$_2$—), 3.87 (s, 3H, CH$_3$O—).

Step 2: Reduction of the product from Step 1 (17 g, 62 mmol) with NiCl$_2$.6H$_2$O/NaBH$_4$ according to the procedure of Preparation 6, step 2, gave the product aniline (6.67 g, 44%). $^1$H Nmr (CDCl$_3$, 400 MHz) δ 7.18 (m, 4H, ArH), 6.82 (m, 2H, ArH), 6.61 (m, 2H, ArH), 3.95 (s, 2H, —CH$_2$—), 3.85 (s, 3H, CH$_3$O—).

Step 3:

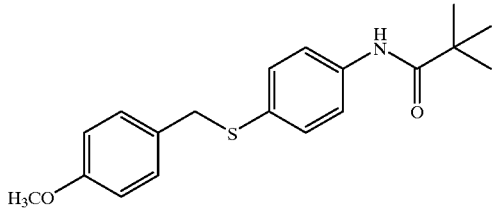

A mixture of the product of Step 2 (6.67 g, 27.2 mmol), trimethylacetyl chloride (5.0 mL, 40 mmol), and DMAP (6.64 g, 54.4 mmol) in CH$_2$Cl$_2$ (100 mL) was stirred for 0.3 h. Then CH$_2$Cl$_2$ (200 mL) was added and the mixture was washed with 1M HCl. The organic layer was dried (Na$_2$SO$_4$), filtered, and evaporated. Recrystallization of the residue from Et$_2$O/hexane/CH$_2$Cl$_2$ afforded the product (4.6 g, 51%) as a white solid. MS (Cl) m/e 330 (M+H)$^+$.

Step 4: To a stirred, ice-cold mixture of the product of Step 3 (500 mg, 1.46 mmol) in CH$_2$Cl$_2$ (25 mL), was added CF$_3$COOH (6 mL) and Hg(OAc)$_2$ (465 mg, 1.46 mmol).

After 1.3 h, the reaction mixture was poured into H₂O, aqueous Na₂S was added, and the mixture was extracted with 1:2 EtOAc/hexanes. The organic layer was dried (Na₂SO₄), filtered, ard evaporated. The residue was subjected to flash chromatography (1:2 EtOAc/hexanes) to give the product (305 mg, 100%). ¹H NMR (CDCl₃, 400 MHz) δ 7.51 (m, 2H, ArH), 7.33 (m, 2H, ArH), 1.49 (s, 311, (CH₃)₃—).

EXAMPLE 1

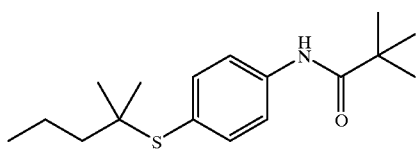

To a mixture of Preparation 1 (10.00 g, 47.7 mmol) and pyridine (7.70 ml, 95.5 mmol) in CH₂Cl₂ (100 ml) was added trimethylacetyl chloride (8.80 ml, 71.6 mmol). The reaction mixture was stirred at RT for 0.5 h, then poured into 2 M HCl (100 ml). The mixture was extracted with CH₂Cl₂ (3×100 ml), dried (Na₂SO₄), filtered, and concentrated. The residue was subjected to flash column chromatography (1:10 EtOAc/hexanes) to afford the title compound (76%). ¹H NMR (CDCl₃, 400 M Hz) δ 7.50–7.39 (m, 4H, ArH), 7.32 (S, 1H, NH), 1.50–1.35 (m, 4H, CH₂CH₂), 1.29 (s, 9H, (CH₃)₃C), 1.17 (s, 6H, (CH₃)₂C), 0.88 (t, 3H, CH₃CH₂). MS (Cl) m/e 294 (M+H)⁺.

Using appropriate starting materials and essentially the same procedure the following compounds can be prepared (Table 1).

TABLE 1

| Ex. | | R¹ | m/e Cl (M + H)⁺ |
|---|---|---|---|
| 1A | | | 280 |
| 1B | | | 404 |
| 1C | | | 309 |
| 1D | | | 343 |
| 1E | | | 292 |

TABLE 1-continued
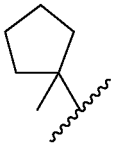
| Ex. | | R¹ | m/e Cl (M + H)⁺ |
|---|---|---|---|
| 1F |  | Ph-N(Me)- | 341 |
| 1G | | (Me)₂N- | 279 |
| 1H | | Ph₂CH- | 402 |
| 1I | 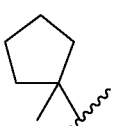 | t-Bu- | 294 |
| 1J | | Ph-N(Me)- | 343 |
| 1K | | (Me)₂N- | 281 |
| 1L | | Ph₂CH- | 404 |
| 1M | 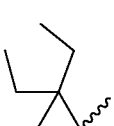 | (Me)₂N- | 253 |

TABLE 1-continued
| Ex. |  | R¹ | m/e Cl (M + H)⁺ |
|---|---|---|---|
| 1N |  |  | 266 |
| 1O |  |  | 376 |
| 1P |  |  | 315 |
| 1Q |  |  | 306 |
| 1R |  |  | 306 |
| 1S |  |  | 320 |
| 1T |  |  | 280 |
| 1U |  |  | 308 |
| 1V | | | 278 |

TABLE 1-continued
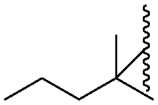
| Ex. | | R¹ | m/e Cl (M + H)⁺ |
|---|---|---|---|
| 1W | 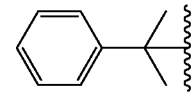 | 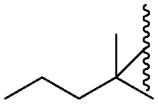 | 356 |
| 1X | 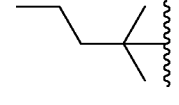 | 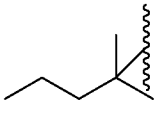 | 322 |
| 1Y | 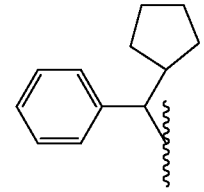 | 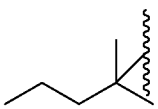 | 396 |
| 1Z | 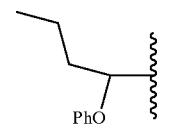 | 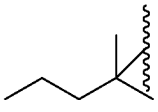 | 386 |
| 1AA | 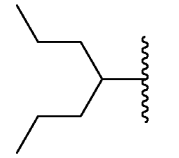 | 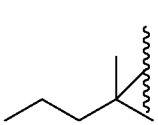 | 336 |
| 1AB | 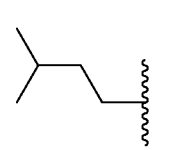 | 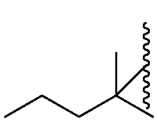 | 308 |
| 1AC | 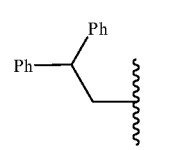 | 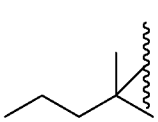 | 418 |
| 1AD | | 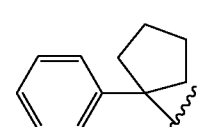 | 382 |

TABLE 1-continued

| Ex. | R¹ | m/e Cl (M + H)⁺ |
|---|---|---|
| 1AE | AcO-C(CH₃)₂-CH₂- | 338 |
| 1AF | cyclohexyl-CH₂- | 320 |
| 1AG | neopentyl-type | 308 |
| 1AH | PhCH(iPr)- | 370 |
| 1AI | 1-phenylcyclopropyl | 354 |
| 1AJ | 2-chlorophenyl-CH₂- | 348 |
| 1AK | 3-chlorophenyl-CH₂- | 348 |
| 1AL | 4-chlorophenyl-CH₂- | 348 |

TABLE 1-continued

| Ex. | R¹ | m/e Cl (M + H)⁺ |
|---|---|---|
| 1AM | | 314 |
| 1AN | | 328 |
| 1AO | | 342 |
| 1AP | | 336 |

EXAMPLE 2

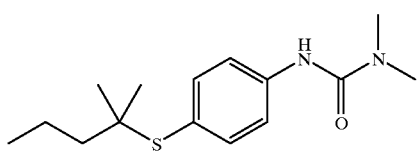

A mixture of Preparation 1 (1.03 g, 4.92 mmol), Et$_3$N (3.40 ml, 24.6 mmol) and triphosgene (0.585 g, 1.97 mmol) in toluene (60 ml) was refluxed for 2 h, then allowed to cool to RT. (CH$_3$)$_2$NH (2.0 M in THF) (4.90 ml, 9.84 mmol) was added. The reaction mixture was allowed to stir at RT for 1.5 h, then poured into cold water. The whole was extracted with CH$_2$Cl$_2$ (3×100 ml), dried (Na$_2$SO$_4$), filtered and concentrated. Purification of the residue by flash chromatography (1:1 EtOAc/hexanes) afforded the title compound (1.03 g, 74%) as a white solid. $^1$H NMR (CDCl$_3$, 400 M Hz) δ 7.43 (m, 4H, ArH), 6.39 (s, 1H, NHCO), 3.07 (s, 6H, N(CH$_3$)$_3$), 1.45 (m, 4H, CH$_2$CH$_2$CMe$_2$S), 1.23 (s, 6H, (CH$_3$)$_2$CS), 0.93 (t, 3H, J=6.88 Hz, CH$_3$CH$_2$). MS (Cl) m/e 281 (M+H)⁺.

Using appropriate starting materials and essentially the same procedure the following compounds can be prepared (Table 2).

TABLE 2

| Ex. | R¹ | m/e Cl (M + H)⁺ |
|---|---|---|
| 2A | | 349 |
| 2B | | 357 |

TABLE 2-continued
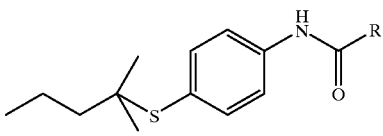
| Ex. | R¹ | m/e Cl (M + H)⁺ |
|---|---|---|
| 2C | 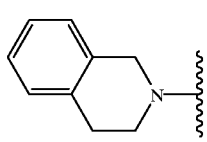 | 379 |
| 2D | 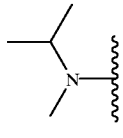 | 369 |
| 2E | 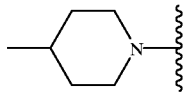 | 309 |
| 2F | 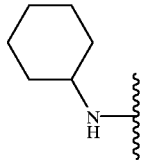 | 335 |
| 2G | 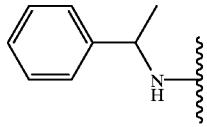 | 335 |
| 2H | 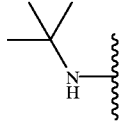 | 357 |
| 2I | 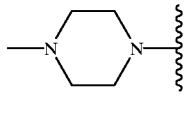 | 309 |
| 2J | 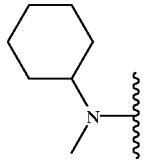 | 336 |
| 2K | 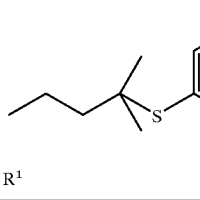 | 363 |
| 2L | 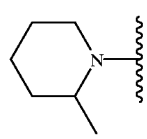 | 339 |
| 2M | 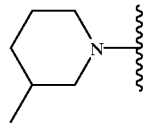 | 335 |
| 2N | 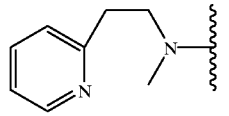 | 335 |
| 2O | 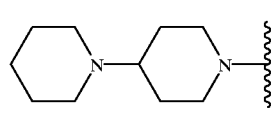 | 372 |
| 2P | 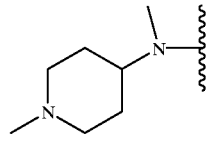 | 404 |
| 2Q | 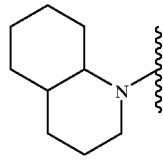 | 364 |
| 2R | 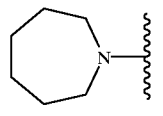 | 375 |
| 2S | 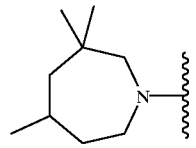 | 335 |
| 2T | | 377 |

TABLE 2-continued

[Structure: pentyl-C(CH3)2-S-C6H4-NH-C(=O)-R1]

| Ex. | R¹ | m/e Cl (M + H)⁺ |
|---|---|---|
| 2U | PhCH2CH2-N(Me)- | 371 |
| 2V | Ph-N(CH2CH2NMe2)- | 414 |
| 2W | n-Pr-N(Me)- | 309 |
| 2X | Me2N-CH2CH2CH2-N(Me)- | 352 |
| 2Y | HO-CH2CH2-N(Me)- | 311 |
| 2Z | (4-pyridyl)-CH2CH2-N(Me)- | 372 |
| 2AA | Me2N-CH2CH2-N(Me)- | 338 |
| 2AB | MeO-CH2CH2-N(Me)- | 325 |
| 2AC | 4-benzyl-piperidin-1-yl | 411 |
| 2AD | cyclohexyl-N(iPr)- | 377 |
| 2AE | Et2N-CH2CH2-N(Me)- | 366 |
| 2AF | imidazol-1-yl-CH2CH2CH2-NH- | 361 |
| 2AG | Me2N-CH2CH2-N(Et)- | 352 |
| 2AH | 1-(EtO2C)-piperidin-4-yl-NH- | 408 |
| 2AI | 1-methyl-piperidin-4-yl-NH- | 350 |
| 2AJ | 4-phenyl-piperazin-1-yl | 398 |

TABLE 2-continued

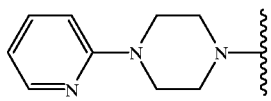

| Ex. | R¹ | m/e Cl (M + H)⁺ |
|---|---|---|
| 2AK | 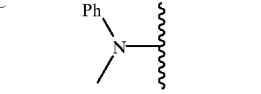 | 399 |

EXAMPLE 3

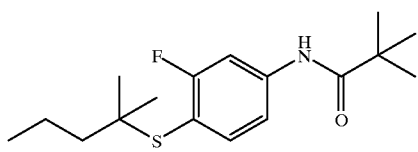

To an ice-cold mixture of Preparation 2 (2.32 g, 9.03 mmol) and NiCl$_2$.6H$_2$O (4.83 g, 20.3 mmol) in CH$_3$OH (100 ml) was added NaBH$_4$ (1.53 g, 40.6 mmol) in portions. After 1.5 h, the reaction mixture was poured into water and the whole was extracted with CH$_2$Cl$_2$ (3×100 ml). The combined organic extracts were dried (Na$_2$SO$_4$), filtered, and concentrated in vacuo to give the desired 3-fluoro-4-(1',1'-dimethylbutylthio)aniline (56%). A mixture of the aniline (60 mg, 0.264 mmol), pyridine (0.11 ml, 1.32 mmol), and (CH$_3$)$_3$CCOCl (0.065 ml, 0.528 mmol) in CH$_2$Cl$_2$ (1.0 ml), was stirred overnight, then subjected to plc (1:6 EtOAc/hexanes) to give the title compound (41%). $^1$H NMR (CDCl$_3$, 400 M Hz) δ 7.65 (m,1H, ArH), 7.45 (m, 2H, ArH & NH), 7.20 (m,1H, ArH), 1.52(m, 4H, CH$_3$CH$_2$CH$_2$), 1.37(s, 9H, C(CH$_3$)$_3$), 1.27(s, 6H, C(CH$_3$)$_2$S), 0.96 (t, 3H, J=6.8 Hz, CH$_3$CH$_2$CH$_2$). MS (Cl) m/e 312 (M+H)⁺. Similarly prepared were compounds of the formula:

| Ex. | R¹ | m/e Cl (M + H)⁺ |
|---|---|---|
| 3A |  | 299 |
| 3B | 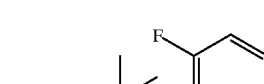 | 422 |

-continued

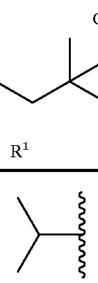

| Ex. | R¹ | m/e Cl (M + H)⁺ |
|---|---|---|
| 3C | 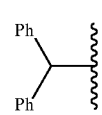 | 361 |

Using the compound of Preparation 3 and the appropriate acid chloride or carbamyl chloride, the procedure of Example 3 afforded the following compounds:

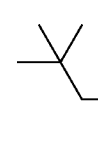

| Ex. | R¹ | m/e Cl (M + H)⁺ |
|---|---|---|
| 3D | 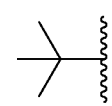 | 314 |
| 3E | 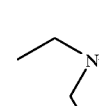 | 438 |
| 3F | 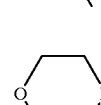 | 342 |
| 3G | 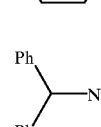 | 328 |
| 3H |  | 343 |
| 3I |  | 357 |
| 3J |  | 439 |

EXAMPLE 4

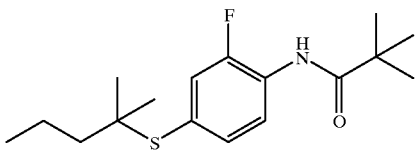

Step 1: A mixture of 2,4-difluoronitrobenzene (2.6 ml, 23.3 mmol), p-methoxybenzyl mercaptan (2.00 g, 11.7 mmol), $K_2CO_3$ (6.47 g, 46.8 mmol) in acetone (50 ml) was refluxed for 20 h. The reaction mixture was poured into cold water. The whole was extracted with $CH_2Cl_2$ (3×100 ml), and the combined organic layers were dried ($Na_2SO_4$), filtered, and concentrated. The residue was purified by flash chromatography (1:30→1:20 EtOAc/hexanes) to give the desired 2-fluoro-4-(4'-methoxybenzylmercapto) nitrobenzene containing a small amount of 4-fluoro-2-(4'-methoxybenzylmercapto)nitrobenzene. MS (Cl) m/e 294 $(M+H)^+$.

Step 2: To a vigorously stirred ice-cold mixture of 2-fluoro-4-(4'-methoxy-benzylmercapto)nitrobenzene and $NiCl_2.6H_2O$ (6.08 g, 25.6 mmol) in $CH_3OH$ was added $NaBH_4$ (1.93 g, 51.1 mmol) in portions. The reaction mixture was stirred for 1 h at 0° C., then poured into cold water. The whole was extracted with $CH_2Cl_2$ (3×100 ml) and the combined organic layers were dried ($Na_2SO_4$), filtered, and evaporated to give 2-fluoro-4-(4'-methoxybenzylmercapto)aniline. MS (Cl) m/e 264 $(M+H)^+$.

Step 3: A mixture of the product of step 2, pyridine (3.1 ml, 38.4 mmol) and $(CH_3)_3CCOCl$ (3.2 ml, 25.6 mmol) in $CH_2Cl_2$ (100 ml) was stirred for 2 h, then poured into cold water. The whole was extracted with $CH_2Cl_2$ (3×100 ml) and the combined organic layers were dried ($Na_2SO_4$), filtered and concentrated to afford 2-fluoro-4-(4'-methoxybenzylmercapto)phenyl-2,2-dimethylpropanamide. MS (Cl) m/e 348 $(M+H)^+$.

Step 4: A solution of the product of Step 3 in $CF_3CO_2H$ (20 ml) was heated at 80° C. for 28 h, then concentrated. The residue (963 mg) was dissolved in $Et_2O$ (2 ml). 2-Methyl-1-pentene (2.0 ml) and concentrated $H_2SO_4$ (0.5 ml) were added with stirring. After 20 min. the reaction mixture was poured into $CH_2Cl_2$ (200 ml), and washed with water and sat'd NaCl. The organic layer was dried ($Na_2SO_4$), filtered and concentrated. The residue was purified by pic (1:10 EtOAc/hexanes) to afford the title compound in 16% overall yield starting from 2,4-difluoronitrobenzene. $^1H$ NMR ($CDCl_3$, 400 MHz) δ 8.37 (t, 1H, J=8.5 Hz, $\underline{ArH}$), 7.71 (s, 1H, $\underline{NH}$), 7.30 (m, 2H, $\underline{ArH}$), 1.50 (m, 4H, $CH_3\underline{CH_2CH_2}$), 1.37 (s, 9H, $C(\underline{CH_3})_3$), 1.25 (s, 6H, $C(\underline{CH_3})_2S$), 0.95 (t, 3H, J=7.0 Hz, $\underline{CH_3}CH_2CH_2$). MS(Cl) m/e 312 $(M+H)^+$.

EXAMPLE 5

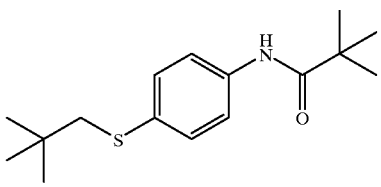

To a refluxing suspension of $FeSO_4.7H_2O$ (3.95 g, 14.2 mmol) and Fe powder (397 mg, 7.1 mmol) in 1:1 $H_2O$/EtOH (100 ml) was added a hot solution of Preparation 4 (319 mg, 1.42 mmol) in EtOH (10 ml). The suspension was refluxed for 6 h, allowed to cool, and filtered through celite. The filtrate was extracted with $CH_2Cl_2$ and the organic extract was dried ($Na_2SO_4$), filtered, and concentrated to afford the aniline (185 mg). A portion of the aniline (30 mg, 0.15 mmol), trimethylacetyl chloride (47 mg, 0.38 mmol), pyridine (62 mg, 0.77 mmol), and 4-dimethylaminopyridine (19 mg, 0.15 mmol) in $CH_2Cl_2$ (2 ml) was stirred overnight. The reaction mixture was subjected to flash chromatography (1:10 EtOAc/hexanes) to afford the title compound (37 mg, 95%) as white solid. MS (Cl) m/e 280 $(M+H)^+$.

EXAMPLE 6

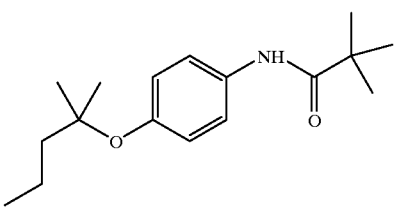

Using the procedure of Example 1, the reaction of Preparation 5 (97 mg, 0.5 mmol) and trimethylacetyl chloride (0.12 ml, 1.0 mmol) afforded the title compound (137 mg, 99%) as a white solid. $^1H$ NMR ($CDCl_3$, 400 MHz) δ 7.43 (2H, m, ArH), 6.97 (2H, m, ArH), 1.64–1.48 (4H, m, $-CH_2CH_2-$), 1.34 (9H, s, $-C(CH_3)_3$), 1.28 (6H, s, $-OC(CH_3)_2-$), 0.97 (3H, t, J=7.1Hz, $-CH_2\underline{CH_3}$). MS (Cl) m/e 278 $(M+H)^+$.

Using appropriate starting materials and essentially the same procedure, the following compounds can be prepared:

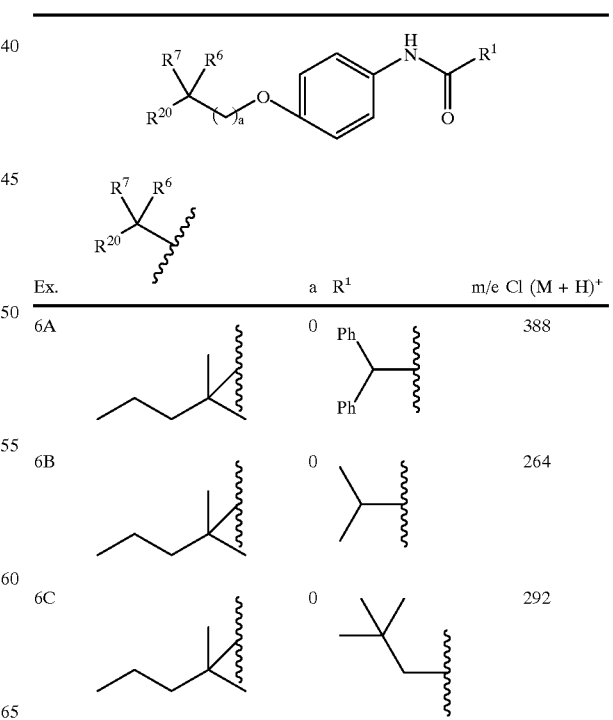

| Ex. | | a | $R^1$ | m/e Cl $(M + H)^+$ |
|---|---|---|---|---|
| 6A | | 0 | Ph, Ph | 388 |
| 6B | | 0 | | 264 |
| 6C | | 0 | | 292 |

-continued

| Ex. | [R20,R7,R6 group] | a | R¹ | m/e Cl (M + H)+ |
|---|---|---|---|---|
| 6D | 1-propylcyclopentyl | 0 | tert-butyl | 304 |
| 6E | 1-propylcyclopentyl | 0 | CHPh₂ | 414 |
| 6F | tert-butyl | 1 | isopropyl | 250 |
| 6G | 1-butylcyclopentyl | 0 | tert-butyl | 318 |
| 6H | 1-butylcyclopentyl | 0 | CHPh₂ | 428 |
| 6I | 1-ethylcyclopentyl | 0 | tert-butyl | 290 |
| 6J | 1-propylcyclopentyl | 0 | CHPh₂ | 400 |
| 6K | tert-butyl | 1 | tert-butyl | 264 |

-continued

| Ex. | [R20,R7,R6 group] | a | R¹ | m/e Cl (M + H)+ |
|---|---|---|---|---|
| 6L | tert-butyl | 1 | CHPh₂ | 374 |
| 6M | 2,2-dimethylbutyl | 0 | NMe₂ | 265 |
| 6N | 1-butylcyclopentyl | 0 | N(Me)Ph | 367 |
| 6O | 2,2-dimethylbutyl | 0 | N(Me)Ph | 327 |
| 6P | 1-propylcyclopentyl | 0 | N(Me)Ph | 353 |
| 6Q | 1-propylcyclopentyl | 0 | NEt₂ | 319 |
| 6R | 1-ethylcyclopentyl | 0 | NEt₂ | 305 |
| 6S | 1-propylcyclopentyl | 0 | N(Me)Ph | 339 |

-continued

| Ex. | (R⁷R⁶R²⁰C-(CH₂)ₐ-) group | a | R¹ | m/e Cl (M + H)⁺ |
|---|---|---|---|---|
| 6T | t-Bu | 1 | N(Et)₂ | 279 |
| 6U | t-Bu | 1 | N(Me)₂ | 251 |
| 6V | t-Bu | 1 | N(Me)(Ph) | 313 |
| 6W | 1-propylcyclopentyl | 1 | t-Bu | 317 |
| 6X | 1-ethylcyclopentyl | 1 | t-Bu | 303 |
| 6Y | 3-methylpent-3-yl | 1 | t-Bu | 277 |
| 6Z | 2-methylpent-2-yl | 1 | t-Bu | 291 |

The following compounds can also be prepared using appropriate starting materials and similar methods:

| Ex. | R¹ | m/e Cl (M + H)⁺ |
|---|---|---|
| 6AA | N(Me)₂ | 299 |
| 6AB | iminodibenzyl (10,11-dihydro-5H-dibenz[b,f]azepin-5-yl) | 449 |
| 6AC | N(Me)(Ph) | 361 |
| 6AD | i-Pr | 298 |
| 6AE | N(i-Pr)₂ | 355 |
| 6AF | CH(Ph)₂ | 422 |
| 6AG | morpholino | 341 |
| 6AH | neopentyl | 326 |
| 6AI | N(H)CH(Ph)₂ | 423 |
| 6AJ | N(Et)₂ | 327 |

EXAMPLE 7

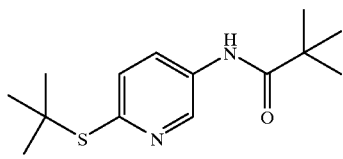

Using the procedure of Example 1, the reaction of the product of Preparation 6 (21 mg, 0.11 mmol) and trimethylacetyl chloride (25 μl, 0.20 mmol) afforded the title compound (20 mg, 65%) as a white solid. $^1$H NMR (CDCl$_3$, 400 MHz) δ 8.59 (1H, s, ArH), 8.17 (1H, d, J=8.6 Hz, ArH), 7.47 (1H, d, J=8.6 Hz, ArH), 1.49 (9H, s, —CO(CH$_3$)$_3$), 1.30 (9H, s, —S(CH$_3$)$_3$). MS (Cl) m/e 267 (M+H)$^+$.

Using appropriate starting materials and essentially the same procedure the following compounds can be prepared:

7A)

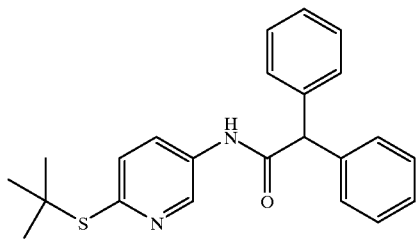

MS (Cl) m/e 377 (M + H)$^+$.

7B)

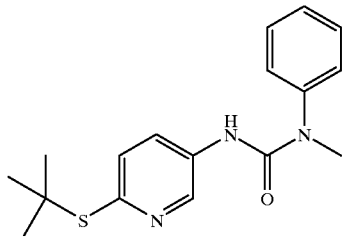

MS (Cl) m/e 316 (M + H)$^+$.

EXAMPLE 8

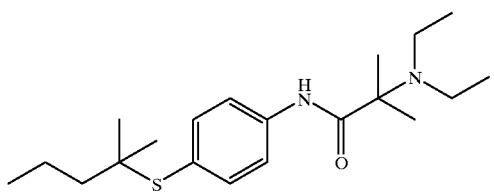

Step 1:

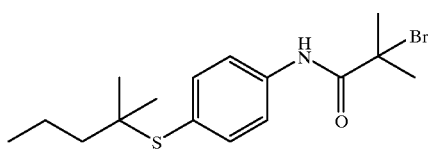
13

To a mixture of Preparation 1 (2.00 g, 9.55 mmol) and pyridine (1.50 ml, 19.1 mmol) in CH$_2$Cl$_2$ (100 ml) was added 2-bromoisobutyryl bromide (1.80 ml, 14.3 mmol). The reaction mixture was stirred at RT for 15 min, then poured into 1N HCl and extracted with CH$_2$Cl$_2$ (3×100 ml). The combined organic layers were dried (Na$_2$SO$_4$), filtered, and concentrated. The residue was subjected to flash chromatography (1:10 EtOAc/hexanes) to afford 13 (99%) as a white solid. $^1$H NMR (CDCl$_3$, 400 MHz) δ 8.55 (s, 1H, NHCO), 7.55 (m, 4H, ArH), 2.10 (s, 6H, (CH$_3$)$_2$CBr), 1.51 (m, CH$_2$CH$_2$), 1.26 (s, 6H, (C$_3$)$_2$CS), 0.96 (t, 3H, CH$_3$CH$_2$). MS (Cl) m/e 358 (M+H)$^+$.

Step 2: To a stirred solution of Et$_2$NH (58 μl, 0.558 mmol) in THF (2.0 ml) was added NaH (8.0 mg, 0.307 mmol), followed by 13 (100 mg, 0.279 mmol). The reaction mixture was stirred at RT for 30 min. and then subjected directly to pic (1:15 EtOAc/hexanes) to afford the title compound (61%). $^1$H NMR (CDCl$_3$, 400 M Hz) δ 9.63 (s, 1H, NHCO), 7.52 (m, 4H, ArH), 2.62 (q, 4H, J=7.15 Hz, N(CH$_2$CH$_3$)$_2$), 1.48 (m, 4H, CH$_2$CH$_2$CMe$_2$S), 1.36 (s, 6H, (CH$_3$)$_2$CN), 1.24 (s, 6H, (CH$_3$)$_2$CS), 1.17 (t, 6H, J=7.09 Hz, N(CH$_2$CH$_3$)$_2$), 0.94 (t, 3H, J=6.88 Hz, CH$_3$(CH$_2$)$_2$CMe$_2$S). MS (Cl) m/e 351 (M+H)$^+$.

Using the same procedure and the appropriate amine, the following compounds were also prepared:

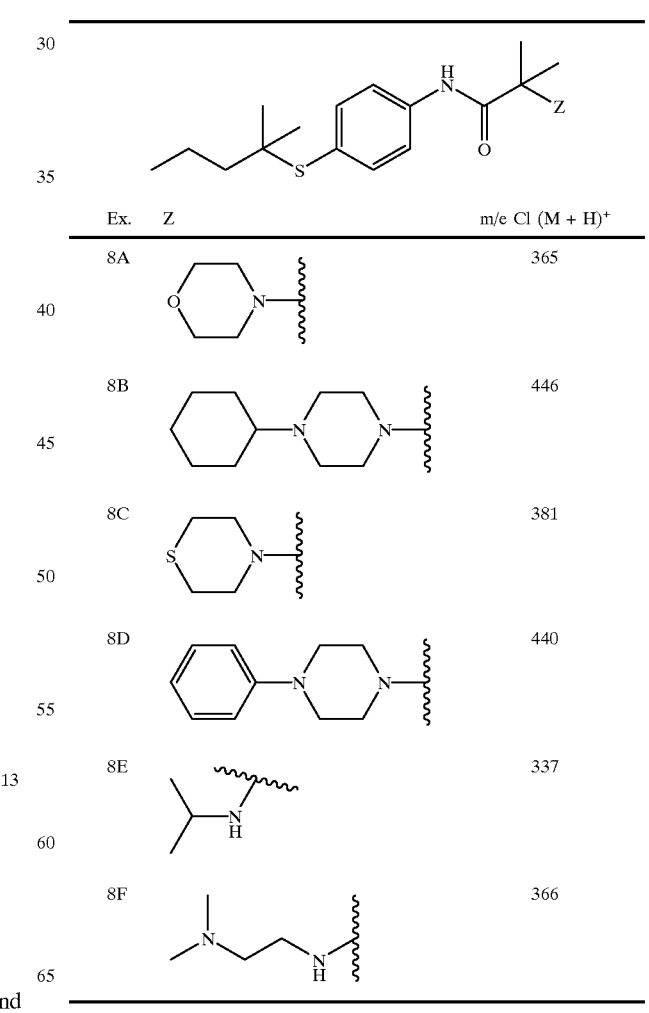

| Ex. | Z | m/e Cl (M + H)$^+$ |
|---|---|---|
| 8A | morpholine | 365 |
| 8B | 4-cyclohexylpiperazine | 446 |
| 8C | thiomorpholine | 381 |
| 8D | 4-phenylpiperazine | 440 |
| 8E | isopropylamine | 337 |
| 8F | N,N-dimethylethylenediamine | 366 |

EXAMPLE 9

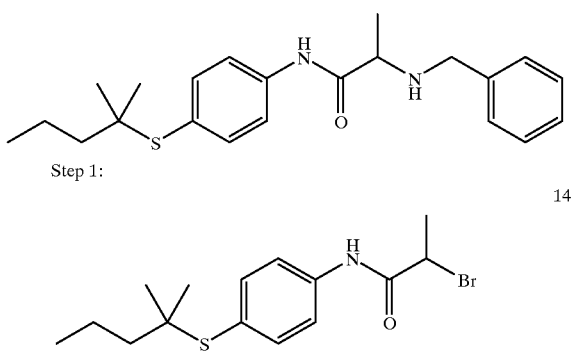

Step 1:

Using the product of Preparation 1 (210 mg, 1.0 mmol) and 2-bromopropionyl bromide (0.10 ml, 1.0 mmol) as starting materials, the procedure described for 13 (Example 8, Step 1) afforded 14 (218 mg, 64%). $^1$H NMR (400 MHz, CDCl$_3$) δ 8.13 (1H, bs, NH), 7.55 (4H, m, ArH), 4.61 (1H, q, J=7 Hz, —CHCH$_3$), 2.03 (3H, d, J=7 Hz, —CHCH$_3$), 1.60–1.45 (4H, m, CH$_2$CH$_2$CH$_3$), 1.26 (6H, s, (CH$_3$)$_2$C), 0.97 (t, 3H, J=7 Hz, CH$_2$CH$_3$).

Step 2: A mixture of 14 (102 mg, 0.30 mmol), benzylamine (65 μl, 0.59 mmol), and K$_2$CO$_3$ (83 mg, 0.60 mmol) in DMSO (1 ml) was stirred. After 2 h, H$_2$O (10 ml) was added and the whole was extracted with CH$_2$Cl$_2$. The combined organic layers were washed with sat'd NaCl, dried (MgSO$_4$), filtered and evaporated. The residue was subjected to pic (1:1 EtOAc/hexanes) to afford the title compound (70 mg, 62%) as a glass. $^1$H NMR (400 MHz, CDCl$_3$) δ 9.60 (1H, bs, NH), 7.62 (2H, m, ArH), 7.52 (2H, m, ArH), 7.48–7.30 (5H, m, ArH), 3.90 (2H, s, CH$_2$Ph), 3.51 (1H, m, —CHCH$_3$), 1.60–1.45 (7H, m, —CHCH$_3$, CH$_2$CH$_2$CH$_3$), 1.26 (6H, s, (CH$_3$)$_2$C), 0.97 (t, 3H, J=7 Hz, CH$_2$CH$_3$). MS (Cl) m/e 371 (M+H)$^+$.

Using the appropriate amine and essentially the same procedures, the following compounds can also be prepared:

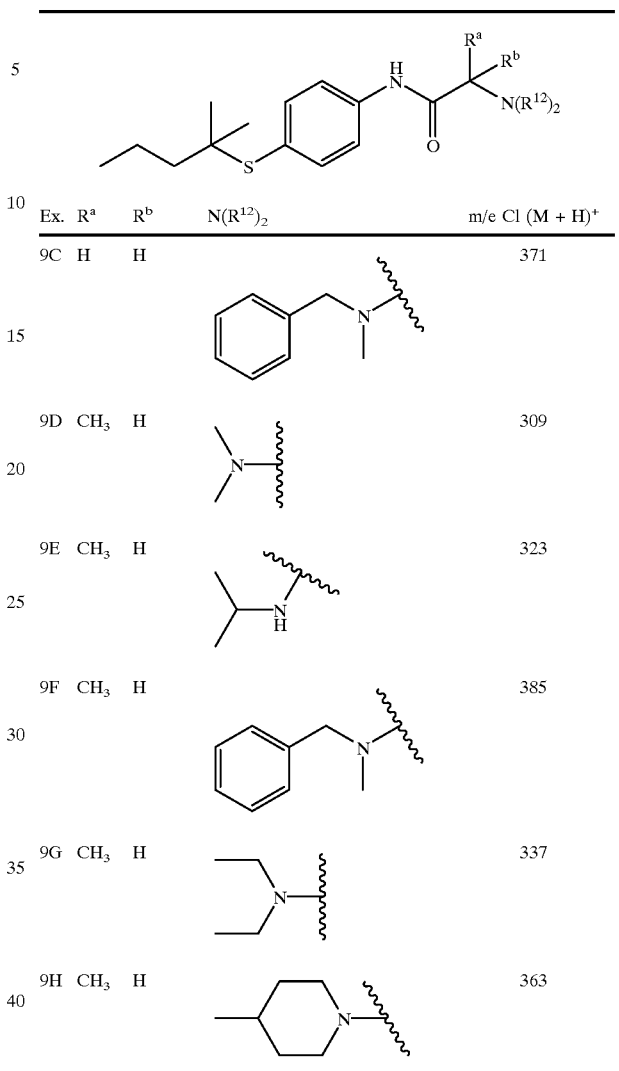

| Ex. | R$^a$ | R$^b$ | N(R$^{12}$)$_2$ | m/e Cl (M + H)$^+$ |
|---|---|---|---|---|
| 9A | H | H | (diethylamino) | 323 |
| 9B | H | H | (benzylamino) | 357 |
| 9C | H | H | (N-methyl-N-benzylamino) | 371 |
| 9D | CH$_3$ | H | (dimethylamino) | 309 |
| 9E | CH$_3$ | H | (isopropylamino) | 323 |
| 9F | CH$_3$ | H | (N-methyl-N-benzylamino) | 385 |
| 9G | CH$_3$ | H | (diethylamino) | 337 |
| 9H | CH$_3$ | H | (4-methylpiperidinyl) | 363 |

EXAMPLE 10

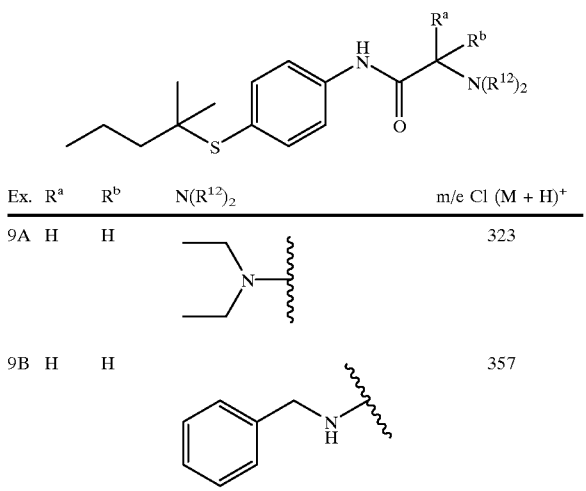

To a solution of Preparation 10 (50 mg, 0.24 mmol) and 3-cyclopentyl-2-methylprop-1-ene (59 mg, 0.48 mmol) in Et$_2$O (0.5 ml) was added conc. H$_2$SO$_4$ (26 μl, 0.48 mmol). The reaction mixture was stirred for 18 h, then subjected to plc (1:6 EtOAc/hexanes) to give the product (28 mg, 35%). $^1$H NMR (CDCl$_3$, 400 MHz) δ 7.57 (m, 4H, ArH), 7.45 (s, 1H, NH), 2.13 (m, 1H, aliphatic H), 1.96 (m, 2H, aliphatic H), 1.62 (m, 4H, aliphatic H), 1.41 (s, 9H, (CH$_3$)$_3$C—), 1.31 (s, 6H, (CH$_3$)$_2$C), 1.19 (m, 4H, aliphatic). MS (Cl) m/e 334 (M+H)$^+$.

Using appropriate starting materials and essentially the same procedure the following compounds are prepared.

10A)

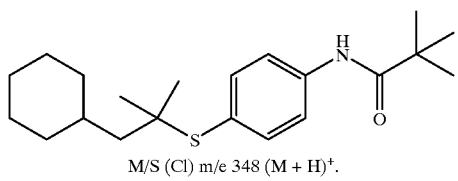

M/S (Cl) m/e 348 (M + H)+.

10B)

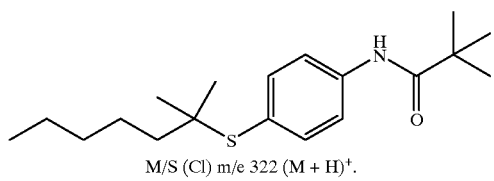

M/S (Cl) m/e 322 (M + H)+.

EXAMPLE 11

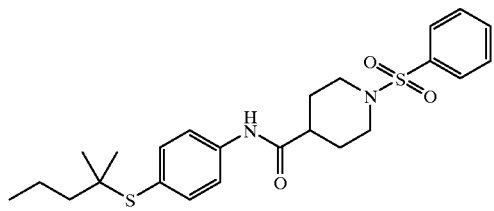

Step 1:

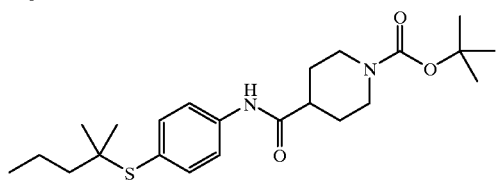

To a mixture of Preparation 1 (2.00 g, 9.56 mmol) and N-t-butoxycarbonylpiperidine-4-carboxylic acid (2.40 g, 10.5 mmol) in DMF (50 ml) was added DMAP (0.082 g, 0.67 mmol) and EDC (1.83 g, 11.6 mmol). The reaction mixture was stirred at RT for 16 h, then partitioned between H$_2$O (300 ml) and EtOAc (300 ml). The organic layer was washed with H$_2$O, dried (MgSO$_4$), filtered, and evaporated. The residue was subjected to flash chromatography (1:5 EtOAc/hexanes) to afford the product (2.16 g, 54%) as a white solid. $^1$H NMR (CDCl$_3$, 400 MHz) δ 7.50 (4H, m, ArH), 7.26 (1H, s, —NH), 4.23 (2H, m, —CH$_2$), 2.83 (2H, m, —CH$_2$), 2.42 (1H, m, —CH), 1.93 (2H, m, —CH$_2$), 1.78 (2H, m, —CH$_2$), 1.50 (9H, s, —C(CH$_3$)$_3$), 1.50–1.42 (4H, m, —(CH$_2$)$_2$—), 1.23 (6H, s, (CH$_3$)$_2$C—), 0.94 (3H, t, J=7.3 Hz, CH$_3$).

Step 2:

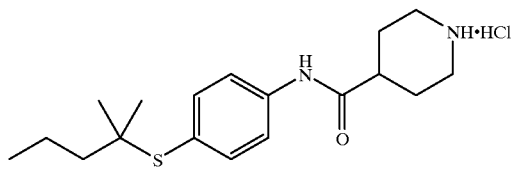

To the product of Step 1 (2.16 g, 5.1 mmol) was added 4M HCl in 1,4-dioxane (70 ml) and the reaction mixture was stirred for 0.5 h. The mixture was concentrated under reduced pressure to afford a white solid (1.80 g) that was used without further purification. $^1$H NMR (CDCl$_3$+ CD$_3$OD, 400 MHz) δ 7.45 (4H, m, ArH), 3.32 (2H, m, —CH$_2$), 3.06 (2H, m, —CH$_2$), 2.71 (1H, m, —CH), 2.02 (2H, m, —CH$_2$), 1.91 (2H, m, —CH$_2$), 1.45–1.32 (4H, m, —(CH$_2$)$_2$—), 1.14 (6H, s, (CH$_3$)$_2$C—), 0.84 (3H, t, J=7.3 Hz, CH$_3$).

Step 3: To a mixture of the product of Step 2 (0.10 g, 0.28 mmol) and Et$_3$N (0.06 ml, 0.43 mmol) in CH$_2$Cl$_2$ (1.5 ml) was added benzenesulfonyl chloride (63 mg, 0.36 mmol). The reaction mixture was stirred for 3 days, then diluted with CH$_2$Cl$_2$. The mixture was washed with 10% NH$_4$OH, 1M HCl, and saturated NaCl, then dried (MgSO$_4$), filtered and evaporated. The residue was subjected to pic (1:99 CH$_3$OH/CH$_2$Cl$_2$) to afford the product (90 mg, 70%) as a white solid. Anal. calcd for C$_{24}$H$_{32}$N$_2$O$_3$S$_2$: C, 62.58; H, 7.00; N, 6.08; S, 13.92. Found: C, 62.20; H, 7.05; N, 6.07; S, 13.72%. MS (FAB) m/e 461 (M+H)+.

Using the appropriate sulfonyl chloride starting material and the procedure of Step 3, the following compounds were prepared:

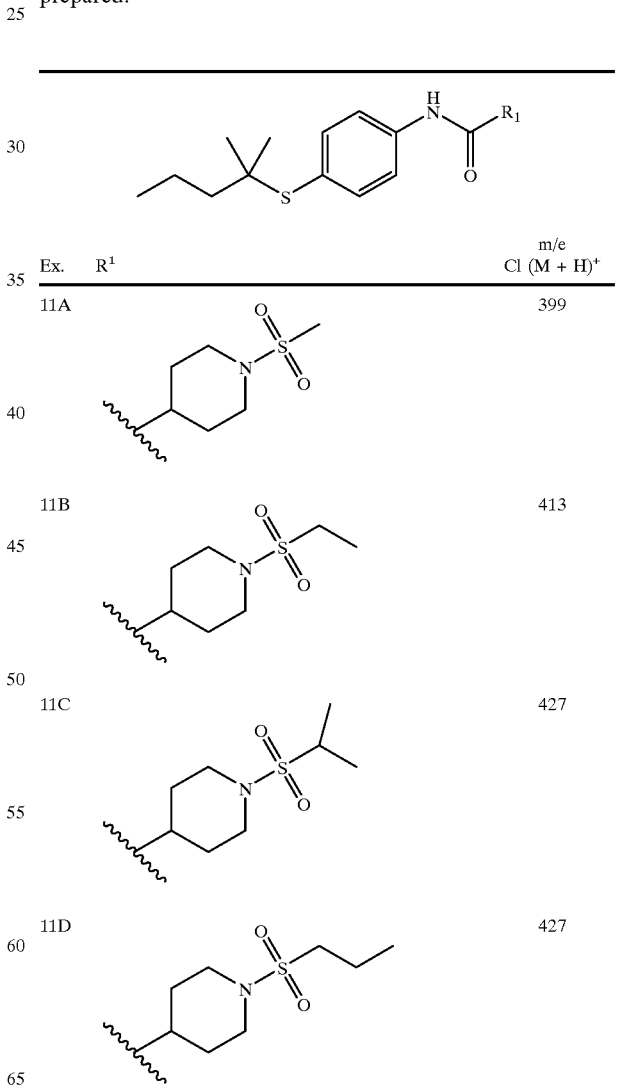

-continued

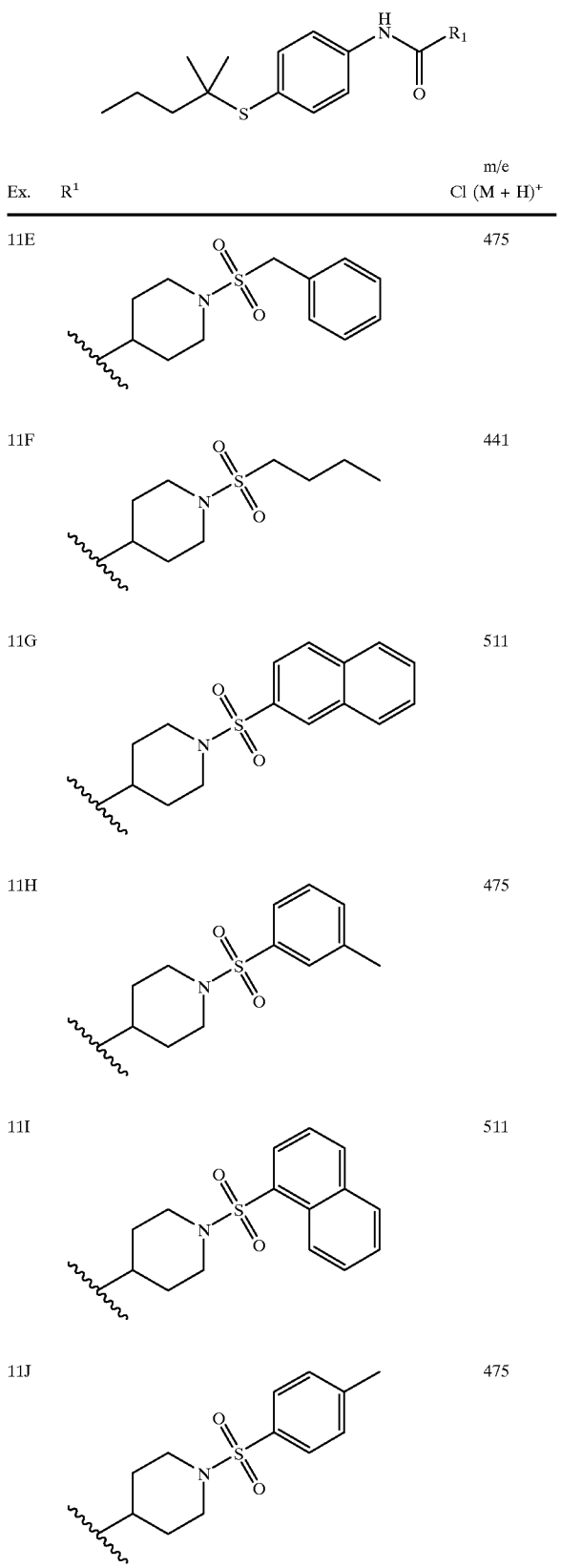

| Ex. | R¹ | m/e Cl (M + H)⁺ |
|---|---|---|
| 11E | | 475 |
| 11F | | 441 |
| 11G | | 511 |
| 11H | | 475 |
| 11I | | 511 |
| 11J | | 475 |

-continued

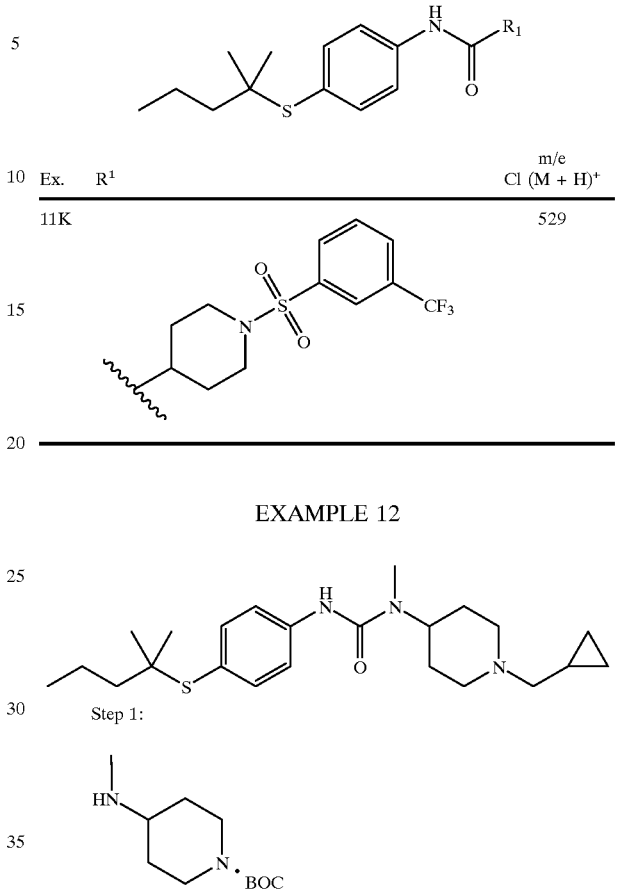

| Ex. | R¹ | m/e Cl (M + H)⁺ |
|---|---|---|
| 11K | | 529 |

EXAMPLE 12

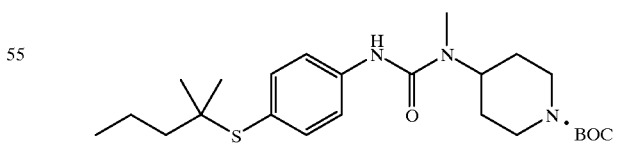

Step 1:

To a mixture of N-t-butoxycarbonyl-4-piperidone (10.0 g, 0.050 mol) and aqueous $CH_3NH_2$ (40% w/w, 10 ml) in 1,2-dichloroethane (125 ml) was added $NaBH(OAc)_3$ (16.0 g, 0.075 mol). The reaction mixture was stirred overnight, then 1M NaOH (250 ml) was added and the whole was extracted with $Et_2O$ (700 ml). The organic layer was washed with sat'd NaCl, dried ($MgSO_4$), filtered, and concentrated to give the product (10.5 g, 97%) as an oil that was used directly in Step 2. $^1H$ NMR ($CDCl_3$, 400 MHz) δ 4.09 (2H, m), 2.86 (2H, m), 2.55 (1H, m), 2.50 (3H, s), 1.90 (2H, m), 1.51 (9H, s), 1.30 (2H, m).

Step 2:

Using the procedure of Example 2, the product of Step 1, triphosgene, and the product of Preparation 1 were reacted to give the product. $^1H$ NMR ($CDCl_3$, 400 MHz) δ 7.32 (4H, m, ArH), 6.32 (1H, s, NH), 4.35 (1H, m, CH), 4.15 (2H, m, $CH_2$), 2.81 (3H, s, $NCH_3$), 2.73 (2H, m, $CH_2$), 1.65–1.32 (8H, m, $CH_2 \times 4$), 1.90 (2H, m), 1.40 (9H, s, $C(CH_3)_3$), 1.13 (6H, s, $(CH_3)_2$), 0.83 (3H, t, J=6.9 Hz, $CH_3$).

Step 3:

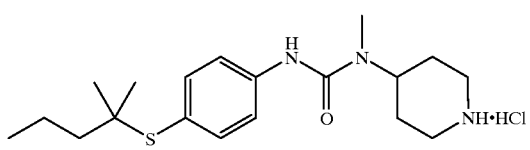

Using the procedure of Example 11, Step 2, the product of Step 2 was reacted with 4M HCl in 1,4-dioxane to give the product. $^1$H NMR (CD$_3$OD, 400 MHz) δ 7.38 (4H, m, ArH), 4.38 (1H, m, CH), 3.50 (2H, m, CH$_2$), 3.12 (2H, m, CH$_2$), 2.96 (3H, s, NCH$_3$), 2.03 (2H, m, CH$_2$), 1.93 (2H, m, CH$_2$), 1.55–1.38 (4H, m, CH$_2$×2), 1.18 (6H, s, (CH$_3$)$_2$), 0.91 (3H, t, J=7.2 Hz, CH$_3$).

Step 4: To a suspension of the product of Step 3 (200 mg, 0.52 mmol) and NaBH(OAc)$_3$ (155 mg, 0.73 mmol) in 1,2-dichloroethane (2.5 ml) was added cyclopropane carboxaldehyde (0.12 ml, 1.6 mmol). After stirring for 16 h, the reaction mixture was added to 1M NaOH (10 ml) and extracted with CH$_2$Cl$_2$ (20 ml). The organic layer was dried (MgSO$_4$), filtered and evaporated. The residue was subjected to plc (1:9 CH$_3$OH/CH$_2$Cl$_2$ saturated with conc. NH$_4$OH) to afford the product (166 mg, 79%) as a white solid. Anal. calcd for C$_{23}$H$_{37}$N$_3$OS: C, 68.44; H, 9.24; N, 10.41; S, 7.94. Found: C, 68.09; H, 9.18; N, 10.36; S, 7.56%. MS (Cl) m/e 404 (M+H)$^+$.

Treatment of the product with excess 1M HCl in Et$_2$O followed by evaporation of the Et$_2$O under reduced pressure gave the HCl salt. Anal. calcd for C$_{23}$H$_{38}$N$_3$OSCl.0.5H$_2$O: C, 61.38; H, 8.96; N, 9.34; S, 7.12. Found: C, 61.72; H, 8.65; N, 9.30; S, 6.81%.

Using the appropriate ketone or aldehyde starting material and the procedure of step 4, the following compounds were prepared:

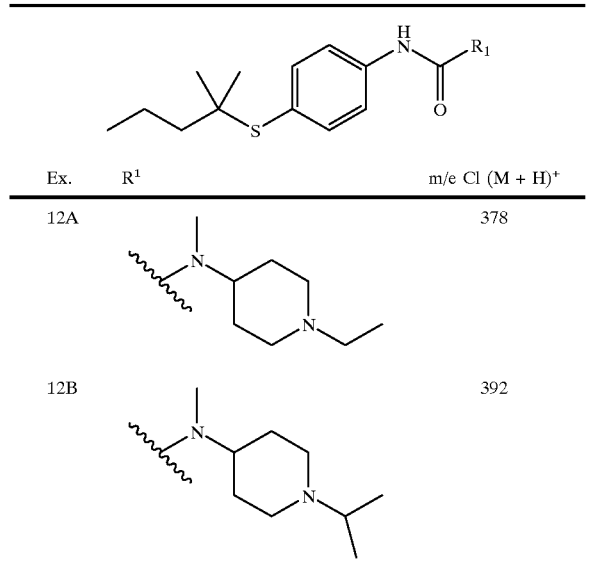

| Ex. | R$^1$ | m/e Cl (M + H)$^+$ |
|---|---|---|
| 12A | | 378 |
| 12B | | 392 |
| 12C | | 440 |
| 12D | | 432 |

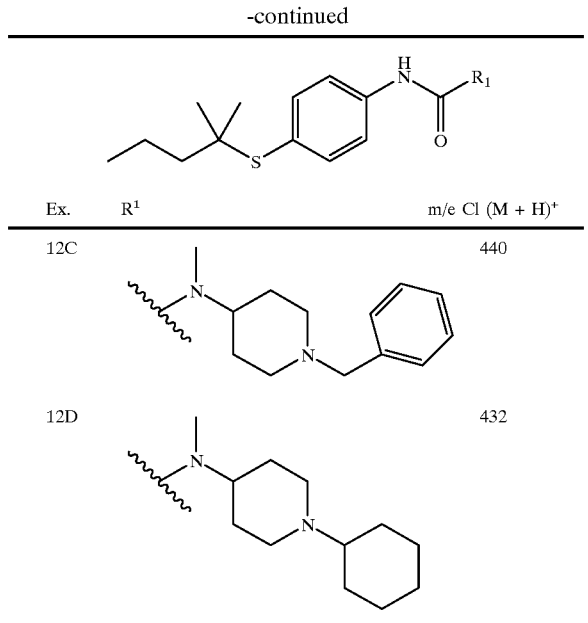

EXAMPLE 13

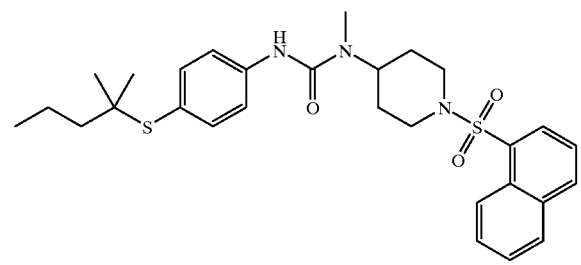

Using the procedure of Example 11, Step 3, reaction of the product of Example 12, Step 3 with 1-naphthalenesulfonyl chloride afforded the product. Anal. calcd for C$_{23}$H$_{37}$N$_3$OS.0.25H$_2$O. C, 64.03; H, 6.90; N, 7.70; S, 11.88. Found: C, 63.75; H, 6.77; N, 7.70; S, 12.05%. MS (Cl) m/e 540 (M+H)$^+$.

Using the appropriate sulfonyl chloride starting material, the following compounds were prepared:

13A)

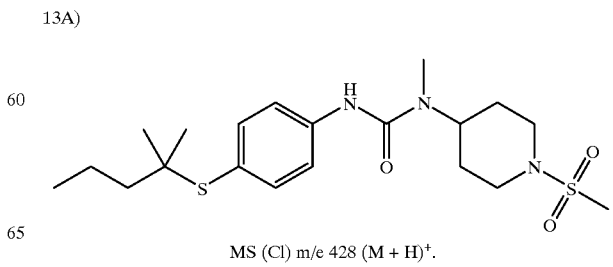

MS (Cl) m/e 428 (M + H)$^+$.

13B)

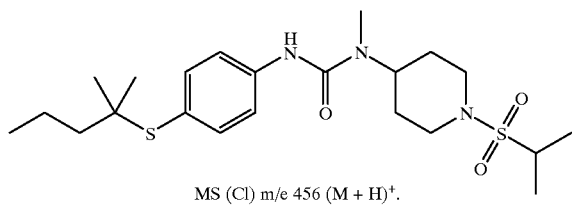

MS (Cl) m/e 456 (M + H)⁺.

13C)

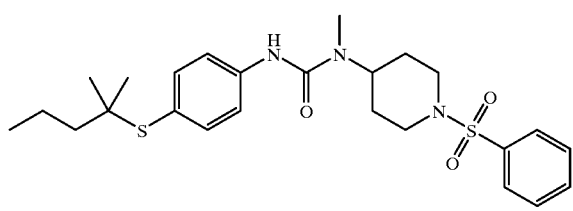

MS (Cl) m/e 490 (M + H)⁺.

EXAMPLE 14

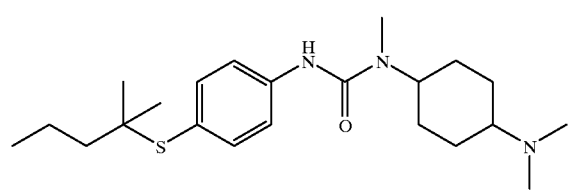

Step 1:

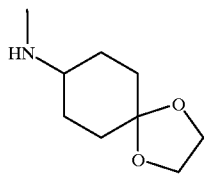

To a stirred mixture of 1,4-cyclohexanedione monoethylene ketal (4.68 g, 30 mmol) and 40% w/w aq. $CH_3NH_2$ (6.0 ml) in 1,2-dichloroethane (75 ml), was added $Na(OAc)_3BH$ (9.6 g, 45 mmol) in portions. The reaction mixture was vigorously stirred for 16 h, then 1N NaOH (75 ml) was added. The organic layer was washed with sat'd NaCl, dried (MgSO₄), filtered and evaporated to give an oil (4.60 g, 90%) that was used without further purification. ¹H NMR (CDCl₃, 400 MHz) δ 3.97 (4H, s), 2.47 (1H, m), 2.46 (3H, s), 1.91 (2H, m), 1.80 (2H, m), 1.59 (2H, m), 1.45 (2H, m).

Step 2:

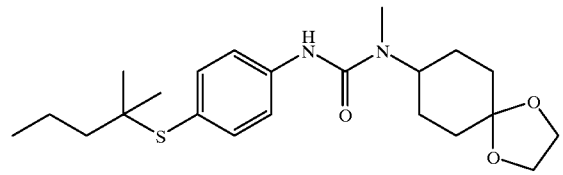

Using the procedure of Example 2, reaction of the product of Step 1 with the isocyanate derived from Preparation 1 afforded the product. MS m/e 407 (M+H)⁺.

Step 3:

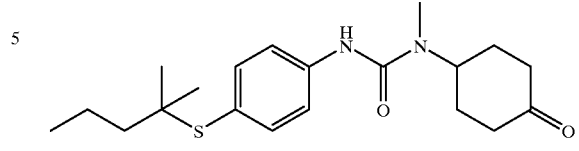

A mixture of the product of Step 2 (1.13 g, 2.8 mmol) and 3M HCl (10 ml) in THF (20 ml) was stirred at RT for 1 h. The reaction mixture was neutralized with 1 M NaOH and extracted with CH₂Cl₂ (2×50 ml). The combined organic layers were dried (MgSO₄), filtered and evaporated. Flash chromatography (1:99 CH₃OH/CH₂Cl₂) of the residue afforded the product (0.90 g, 88%). MS m/e 363 (M+H)⁺.

Step 4: To a stirred mixture of the product of Step 3 (100 mg, 0.28 mmol) and 40% w/w (CH₃)₂NH (0.09 ml, 0.9 mmol) in CH₂Cl₂ (1 ml) was added Na(OAc)₃BH (88 mg, 0.42 mmol). After 16 h, 1M NaOH (5 ml) was added and the whole was extracted with CH₂Cl₂ (2×10 ml). The combined organic layers were dried (MgSO₄), filtered, and concentrated. Purification of the residue by preparative tlc (1:7:92 conc. NH₄OH/CH₃OH/CH₂Cl₂) afforded the less polar cis isomer, 14A (48 mg, 45%) and the more polar trans isomer, 14B (31 mg, 29%).

14A, Cis isomer

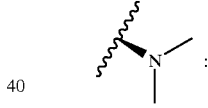

¹H NMR (CDCl₃+CD₃OD, 400 MHz) δ 7.22 (4H, m), 4.08 (1H, m), 2.79 (3H, s), 2.13 (6H, s), 2.08 (1H, m), 1.83 (2H, m), 1.60 (2H, m), 1.40–1.23 (8H, m), 1.03 (6H, s), 0.74 (3H, t, J=7.3 Hz). MS m/e 392 (M+H)⁺.

14B, Trans isomer

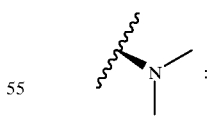

¹H NMR (CDCl₃+CD₃OD, 400 MHz) δ 7.22 (4H, m), 3.92 (1H, m), 2.72 (3H, s), 2.13 (6H, s), 1.96 (1H, m), 1.93 (2H, m), 1.63 (2H, m), 1.45–1.22 (8H, m), 1.04 (6H, s), 0.74 (3H, t, J=7.2 Hz). MS m/e 392 (M+H)⁺.

Using the appropriate amine and essentially the same procedure outlined in Example 14, Step 4, the following compounds were prepared.

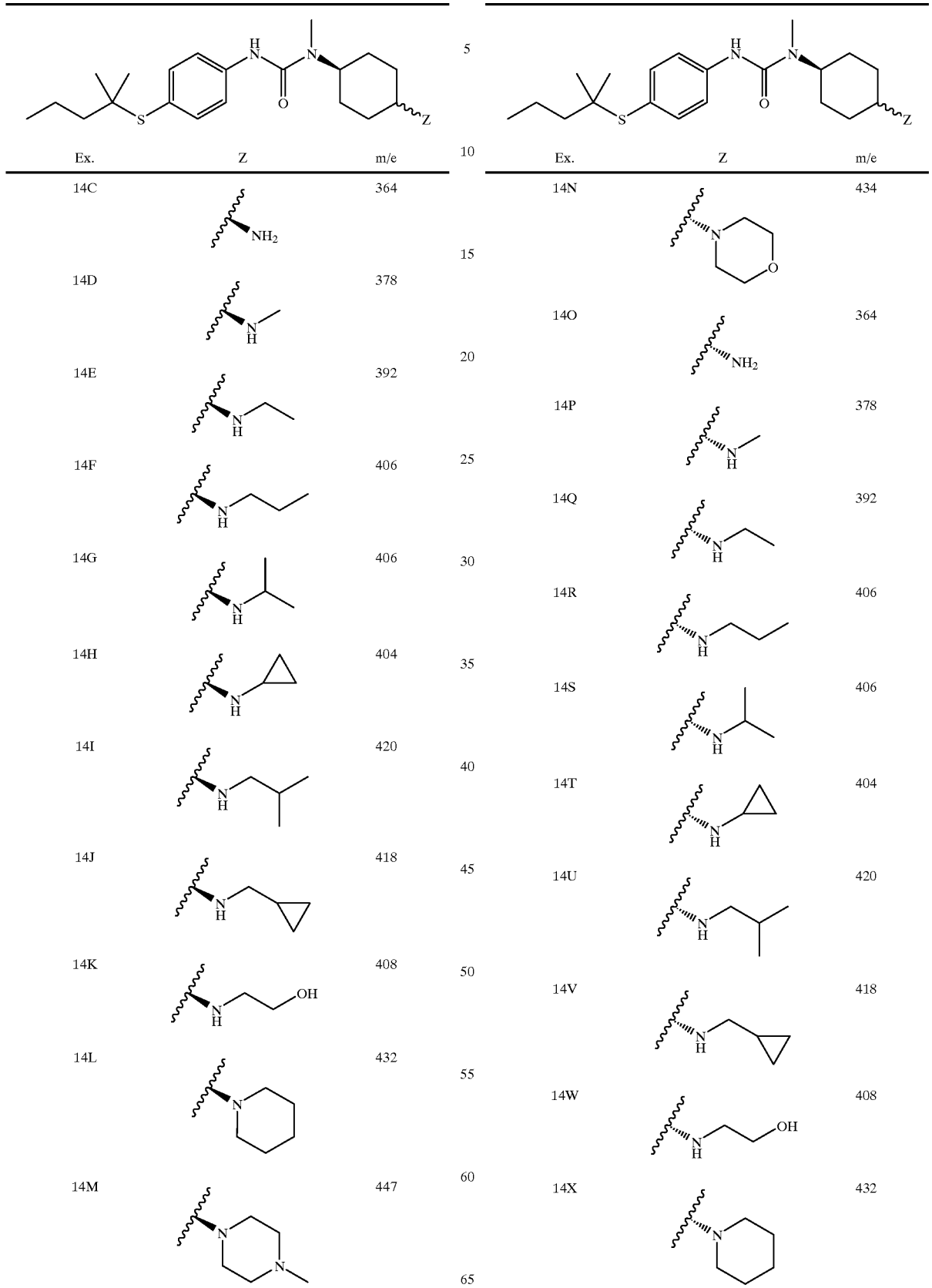

-continued

| Ex. | Z | m/e |
|---|---|---|
| 14Y | 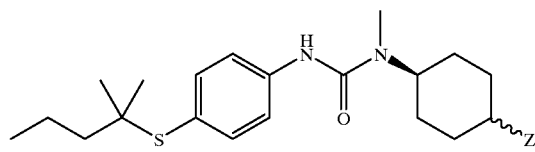 | 447 |

EXAMPLE 15

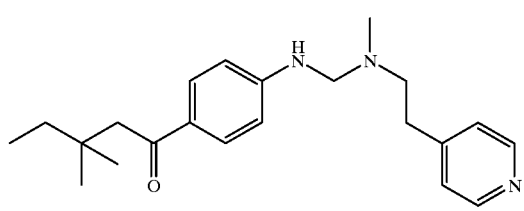

Using the procedure of Example 2, Preparation 7, Pr$_2$NEt, triphosgene, and 4-(2-methylamino)ethylpyridine were reacted to give the product. $^1$H NMR (CDCl$_3$, 400 MHz) δ 8.50 (2H, s, ArH), 7.85 (2H, m, ArH), 7.41 (2H, m, ArH), 7.19 (2H, m, ArH), 6.60 (1H, s, NH), 3.60 (2H, t, J=6.8 Hz, CH$_2$N), 2.97 (3H, s, CH$_3$N), 2.95 (2H, t, J=7.2 Hz, NCH$_2$CH$_2$), 2.77 (2H, s, CH$_2$CO), 1.40 (2H, q, J=7.6 Hz, CH$_3$CH$_2$), 1.03 (6H, s, (CH$_3$)$_2$C), 0.85 (3H, t, J=7.6 Hz, CH$_3$CH$_2$). MS (ES) m/e 368 (M+H)$^+$.

Reaction of Preparation 7, 8, or 9, triphosgene, and the appropriate amine by essentially the same procedure afforded the following compounds:

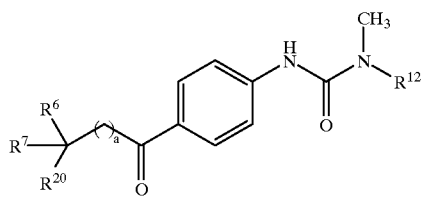

wherein a, R$^6$, R$^7$, R$^{20}$ and R$^{12}$ are as defined in the table

| Ex. | R$^6$ R$^7$ R$^{20}$ | a | R$^{12}$ | MS m/e (M + H) |
|---|---|---|---|---|
| 15A | 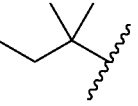 | 0 | 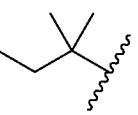 | 368 |
| 15B | 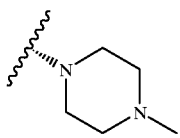 | 0 | | 368 |

-continued
| Ex. | 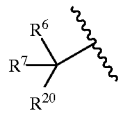 R⁶, R⁷, R²⁰ | a | R¹² | MS m/e (M + H) |
|---|---|---|---|---|
| 15C | 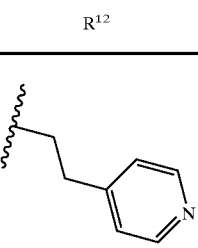 | 0 | 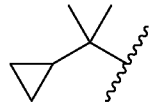 | 366 |
| 15D | 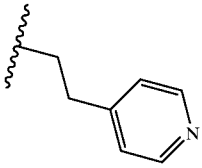 | 0 | 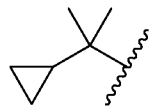 | 366 |
| 15E | 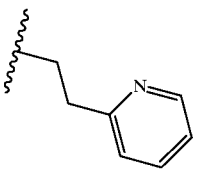 | 0 | 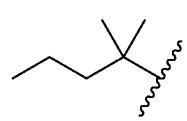 | 360 |
| 15F | 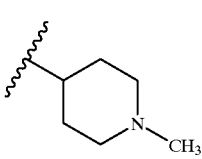 | 1 | 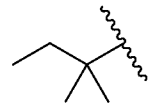 | 360 |
| 15G | 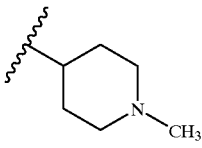 | 0 | 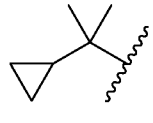 | 358 |
| 15H | 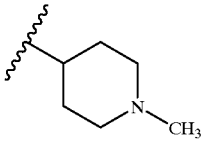 | 0 | 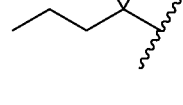 | 446 |
| 15I | 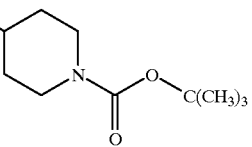 | 1 | 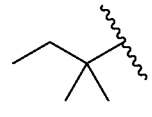 | 446 |

| Ex. | $R^6$ $R^7$ $R^{20}$ | a | $R^{12}$ | MS m/e (M + H) |
|---|---|---|---|---|
| 15J | 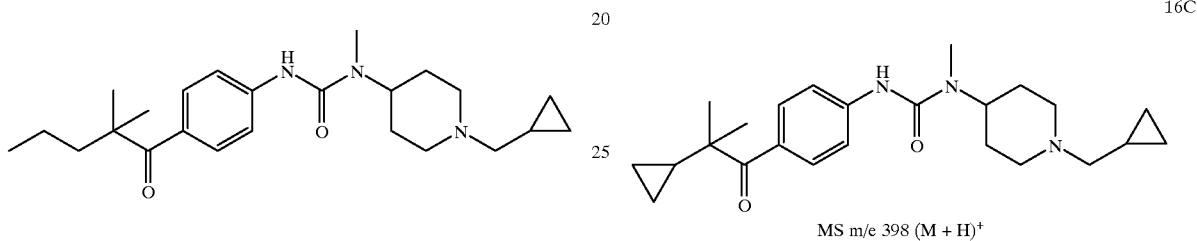 | 0 | | 444 |

EXAMPLE 16

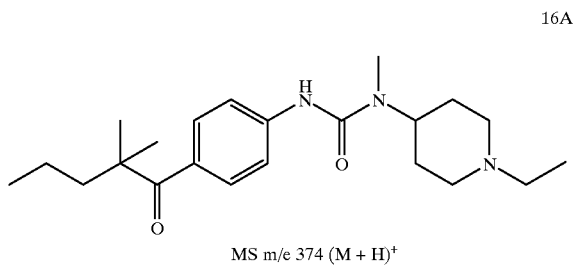

Step 1: Using the procedure described in Example 11, Step 2, the compound of Example 15H was treated with HCl to obtain the hydrochloride. MS m/e 346 (M−Cl)⁺.

Step 2: Using the procedure described in Example 12, Step 4, cyclopropane carboxaldehyde was reacted with the product of Step 1 to obtain the title compound. MS m/e 400 (M+H)⁺.

Using the appropriate starting materials and essentially the same procedure, the following compounds were prepared:

16A

MS m/e 374 (M + H)⁺

16B

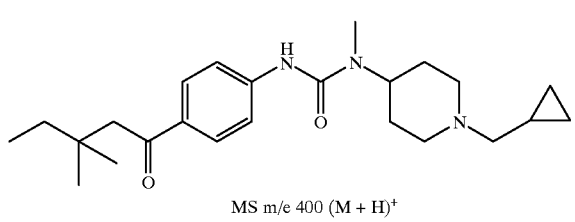

MS m/e 400 (M + H)⁺

16C

MS m/e 398 (M + H)⁺

EXAMPLE 17

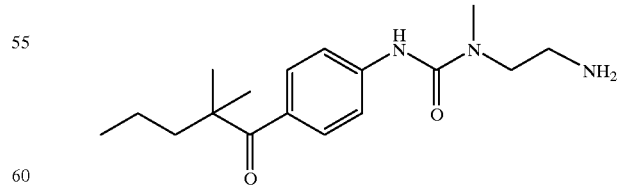

Step 1: To a mixture of t-butyldiphenylchlorosilane (9.3 g, 34 mmol) and Et₃N (5.12 g, 51 mmol) in CH₃CN (50 ml) was slowly added N-methylethylenediamine (5.0 g, 67 mmol). The reaction mixture was stirred for 2 h. After removal of CH₃CN, the residue was dissolved in CH₂Cl₂ and washed with sat'd NaHCO₃ and H₂O. The organic layer was dried (MgSO₄), filtered and evaporated to give a colorless oil (10.2 g) which was used directly in Step 2.

Step 2:

Using the procedure of Example 2, reaction of Preparation 8, triphosgene, and the product of Step 1 afforded the product. MS m/e 306.1 (M+H)⁺.

Step 3: To a solution of the product of Step 2 (95 mg, 0.31 mmol) and Et₃N (63 mg, 0.62 mmol) in CH₂Cl₂ (2 ml) was added CH₃SO₂Cl (72 mg, 0.63 mmol) dropwise. After 5 min, the reaction mixture was subjected to preparative TLC (CH₂Cl₂/CH₃OH/conc. NH₄OH 10:1:0.1) to afford the product (70 mg, 59%). ¹HNMR (CDCl₃, 400 MHz) δ 7.76 (2H, m, ArH), 7.47 (2H, m, ArH), 7.20 (1H, s, NH), 5.90 (1H, bs, NH), 3.50 (2H, m, C$\underline{H_2}$CH₂), 3.30 (2H, m, CH₂C$\underline{H_2}$), 2.98 (3H, s, CH₃), 2.97 (s, 3H, CH₃), 1.70 (m, 2H, C$\underline{H_2}$), 1.05–1.4 (8H, m, (CH₃)₂ & CH₂), 0.9 (t, 3H, J=7.3 Hz, CH₃). MS m/e 384.1 (M+H)⁺.

EXAMPLE 18

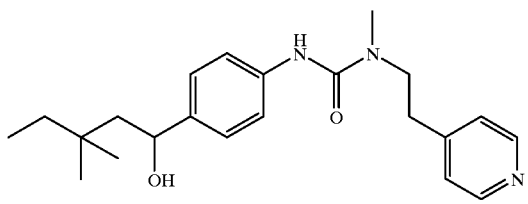

To a solution of Example 15 (330 mg, 0.90 mmol) in CH₃OH (10 ml) at RT was added NaBH₄ (68 mg, 18 mmol) in portions. The reaction was stirred at room temperature for 2 h, then poured into sat.'d NaHCO₃. The whole was extracted with CH₂Cl₂ (3×50 ml), the combined organic layers were washed with H₂O and brine, dried (Na₂SO₄), filtered and concentrated. The crude product (230 mg, 69%) was used in the next step without further purification. ¹H NMR (CDCl₃, 400 MHz) δ 8.50 (2H, br, A$\underline{rH}$), 7.10–7.30 (6H, m, A$\underline{rH}$), 6.30 (1H, s, N$\underline{H}$), 4.75 (1H, m, HOC$\underline{H}$), 3.60 (2H, t, J=7.2 Hz, C$\underline{H_2}$N), 2.93 (3H, s, C$\underline{H_3}$N), 2.88 (2H, t, J=7.6 Hz, NCH₂C$\underline{H_9}$), 2.22 (1H, br, O$\underline{H}$), 1.70 (1H, m, HOCHC$\underline{Ha}$Hb), 1.50 (1H, m, HOCHCHa$\underline{Hb}$), 1.31 (m, 2H, CH₃C$\underline{H_2}$), 0.89 (6H, s, ($\underline{CH_3}$)₂C), 0.80 (3H, t, J=7.2 Hz, C$\underline{H_3}$CH₂).

Use of the appropriate starting material and essentially the same procedure afforded the following compounds:

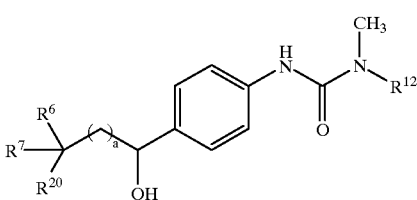

wherein a, R⁶, R⁷, R²⁰ and R¹² are as defined in the table

| Ex. | R⁶ R⁷ R²⁰ | a | R¹² | MS m/e (M+H) |
|---|---|---|---|---|
| 18A | ![] | 0 | 4-pyridylethyl | 370 |
| 18B | ![] | 0 | 2-pyridylethyl | 370 |
| 18C | ![] | 0 | (1-methylpiperidin-4-yl)methyl | 362 |
| 18D | ![] | 1 | (1-methylpiperidin-4-yl)methyl | 362 |

-continued
| Ex. | R6, R7, R20 | a | R12 | MS m/e (M + H) |
|---|---|---|---|---|
| 18E | 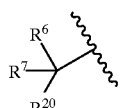 | 1 |  | 402 |
| 18F | 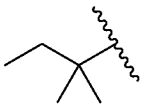 | 0 | 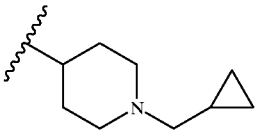 | 402 |
| 18G | 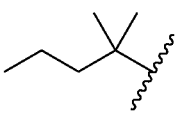 | 0 | 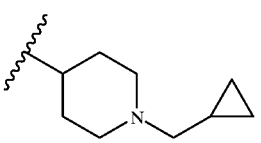 | 376 |
| 18H | 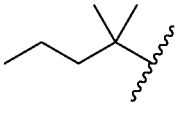 | 0 | 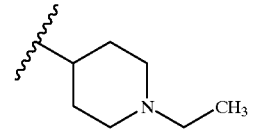 | 368 |
| 18I | 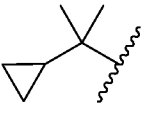 | 0 | 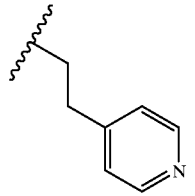 | 368 |
| 18J | 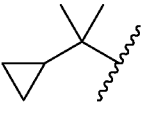 | 0 | 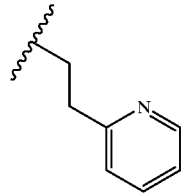 | 360 |
| 18K | 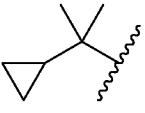 | 0 | 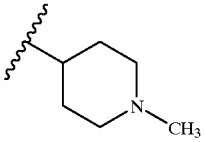 | 400 |
| 18L | 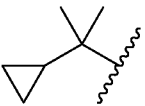 | 0 | 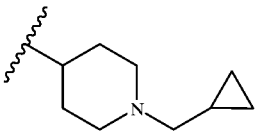 | 386 |

EXAMPLE 19

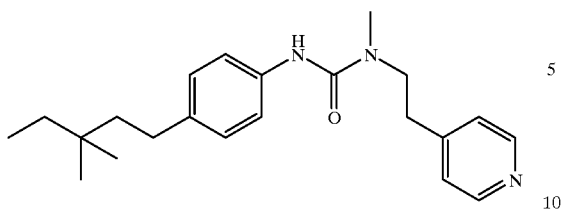

To a solution of Example 18 (230 mg, 0.62 mmol) in dry CH$_2$Cl$_2$ (20 ml) was added Et$_3$SiH (723 mg, 6.2 mmol) and CF$_3$CO$_2$H (142 mg, 1.2 mmol). The reaction mixture was stirred at RT for 16 h, then concentrated. The residue was subjected to preparative TLC (1:10 (2M NH$_3$ in CH$_3$OH)/CH$_2$Cl$_2$) to afford the product (180 mg, 82%) as colorless oil. $^1$H NMR (CDCl$_3$, 400 MHz) δ 8.50 (2H, m, ArH), 7.0–7.25 (6H, m, ArH), 6.20 (1H, s, NH), 3.60 (2H, t, J=7.2 Hz, CH$_2$N), 2.94 (3H, s, CH$_3$N), 2.85 (2H, t, J=7.2 Hz, CH$_2$CH$_2$N), 2.45 (2H, m, CH$_2$CH$_2$CMe$_2$), 1.40 (2H, m, CH$_2$CH$_2$CMe$_2$), 1.30 (2H, q, J=7.2 Hz, CH$_3$CH$_2$), 0.88 (6H, s, C(CH$_3$)$_2$), 0.80 (3H, t, J=7.6 Hz, CH$_3$CH$_2$). MS (ES) m/e 354 (M+H)$^+$.

Using appropriate starting materials and essentially the same procedure the following compounds were prepared:

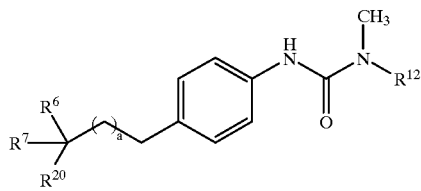

wherein a, R$^6$, R$^7$, R$^{20}$ and R$^{12}$ are as defined in the table

| Ex. | R$^6$, R$^7$, R$^{20}$ | a | R$^{12}$ | ME m/e (M+H) |
|---|---|---|---|---|
| 19A | (2,2-dimethylbutyl branched) | 0 | 2-(pyridin-4-yl)ethyl | 354 |
| 19B | (2,2-dimethylbutyl branched) | 0 | 2-(pyridin-4-yl)ethyl | 354 |
| 19C | (2,2-dimethylbutyl branched) | 0 | (1-methylpiperidin-4-yl)methyl | 346 |
| 19D | (tert-butyl branched) | 1 | (1-methylpiperidin-4-yl)methyl | 386 |
| 19E | (tert-butyl branched) | 1 | (1-(cyclopropylmethyl)piperidin-4-yl)methyl | 386 |

-continued
| Ex. | R⁶ R⁷ R²⁰ | a | R¹² | ME m/e (M + H) |
|---|---|---|---|---|
| 19F | 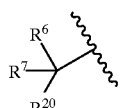 | 0 |  | 386 |
| 19G | 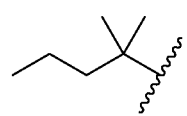 | 0 | 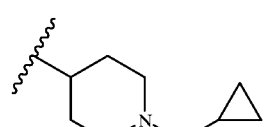 | 360 |
| 19H | 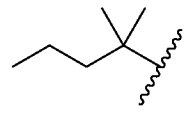 | 0 | 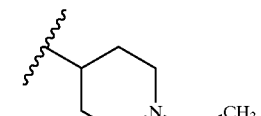 | 352 |
| 19I | 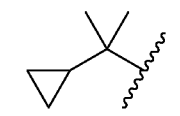 | 0 | 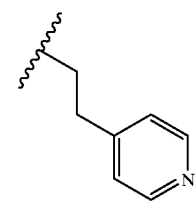 | 352 |
| 19J | 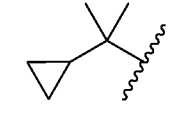 | 0 | 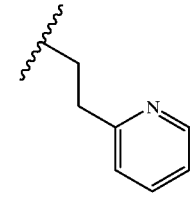 | 344 |
| 19K | 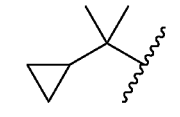 | 0 | 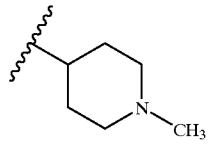 | 384 |
| 19L | 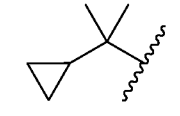 | 0 | 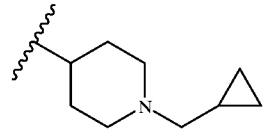 | 370 |
| 19M | 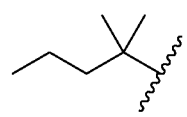 | 1 | 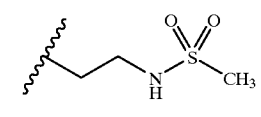 | — |

-continued

| Ex. | R⁶ R⁷ R²⁰ | a | R¹² | ME m/e (M+H) |
|---|---|---|---|---|
| 19N | 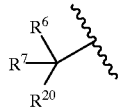 | 1 | 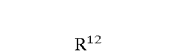 | — |
| 19O |  | 1 | 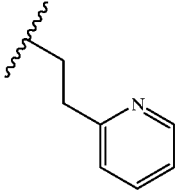 | — |

EXAMPLE 20

Step 1:

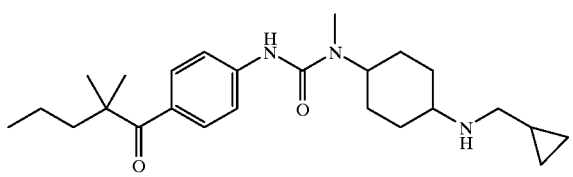

Reaction of Preparation 8 with the product of Example 14, Step 1 according to the procedure of Example 2 afforded the product. ¹H NMR (CDCl₃, 400 MHz) δ 7.76 (2H, m), 7.42 (2H, m), 6.48 (1H, s), 4.28 (1H, m), 3.95 (4H, s), 2.91 (3H, s), 1.75 (10H, m), 1.30 (6H, s), 1.21 (2H, m), 0.83 (3H, t). MS m/e 403 (M+H)⁺.

Step 2:

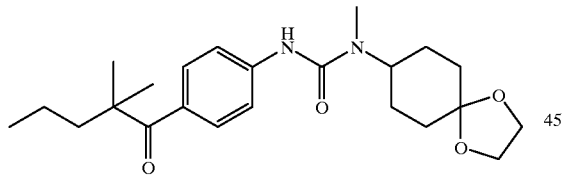

Reaction of the product of Step 1 with HCl by the procedure of Example 14, Step 3, afforded the product. ¹H NMR (CDCl₃, 400 MHz) δ 7.77 (2H, m), 7.44 (2H, m), 6.58 (1H, s), 4.81 (1H, m), 2.91 (3H, s), 2.57 (2H, m) 2.46 (2H, m), 2.03 (2H, m), 1.90 (2H, m), 1.75 (2H, m), 1.30 (6H, s), 1.21 (2H, m), 0.83 (3H, t). MS m/e 359 (M+H)⁺.

Step 3: Reaction of the product of Step 2 with cyclopropanemethylamine by the procedure of Example 14, Step 4, afforded the product as a mixture of cis and trans isomers that was separated by preparative tlc (1:9 (2M NH₃ in CH₃OH)/CH₂Cl₂).

20A, less polar Cis isomer

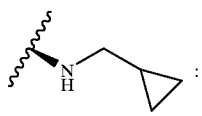

¹H NMR (CDCl₃, 400 MHz) δ 7.75 (2H, m), 7.44 (2H, m), 6.58 (1H, s), 4.14 (1H, m), 2.94 (3H, s), 2.93 (1H, m), 2.46 (2H, m), 1.85 (4H, m), 1.74 (2H, m), 1.59 (2H, m), 1.46 (2H, m), 1.29 (6H, s), 1.20 (2H, m), 0.98 (1H, m), 0.82 (3H, t, J=7.2 Hz), 0.51 (2H, m), 0.14 (2H, m). MS m/e 414 (M+H)⁺.

20B, more polar trans isomer

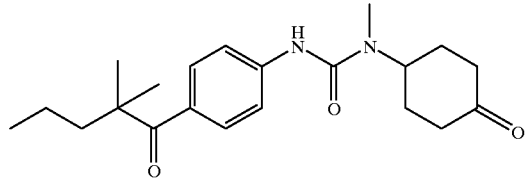

¹H NMR (CDCl₃, 400 MHz) δ 7.75 (2H, m), 7.45 (2H, m), 6.64 (1H, s), 4.16 (1H, m), 2.89 (3H, s), 2.50 (3H, m), 2.05 (2H, m), 1.74 (4H, m,), 1.51 (2H, m), 1.38 (2H, m), 1.29 (6H, s), 1.23 (2H, m), 0.98 (1H, m), 0.82 (3H, t, J=7.3 Hz), 0.49 (2H, m), 0.15 (2H, m). MS m/e 414 (M+H)⁺.

Similarly prepared from the product of Step 2 were:

20C

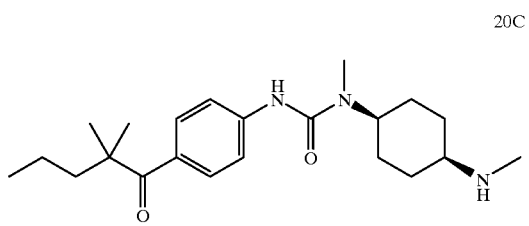

¹H NMR (CDCl₃, 400 MHz) δ 7.77 (2H, m), 7.42 (2H, m), 6.50 (1H, s), 4.14 (1H, m), 2.93 (3H, s), 2.72 (1H, m), 2.39 (3H, s), 1.84 (4H, m), 1.76 (2H, m), 1.59 (2H, m), 1.46 (2H, m), 1.30 (6H, s), 1.21 (2H, m), 0.82 (3H, t, J=7.2 Hz). MS m/e 374 (M+H)⁺.

20D

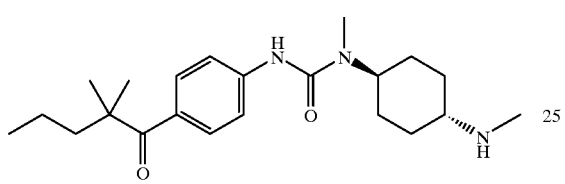

¹H NMR (CDCl₃, 400 MHz) δ 7.76 (2H, m), 7.42 (2H, m), 6.48 (1H, s), 4.17 (1H, m), 2.89 (3H, s), 2.44 (3H, s), 2.35 (1H, m), 2.05 (2H, m), 1.75 (4H, m), 1.50 (2H, m), 1.46 (2H, m), 1.30 (6H, s), 1.21 (2H, m), 0.83 (3H, t, J=7.3 Hz). MS m/e 374 (M+H)⁺.

20E

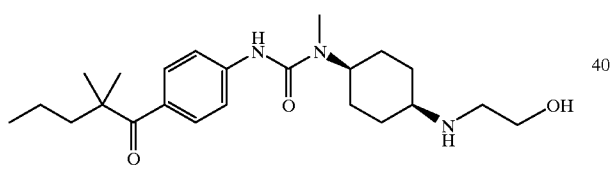

¹H NMR (CDCl₃, 400 MHz) δ 7.75 (2H, m), 7.43 (2H, m), 6.51 (1H, s), 4.14 (1H, m), 3.70 (2H, m), 2.93 (3H, s), 2.80 (2H, m), 2.52 (1H, m), 1.88 (4H, m), 1.75 (2H, m), 1.71 (2H, m), 1.51 (2H, m), 1.30 (6H, s), 1.21 (2H, m), 0.83 (3H, t, J=7.3 Hz). MS m/e 404 (M+H)⁺.

20F

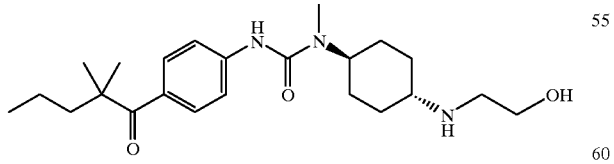

¹H NMR (CDCl₃, 400 MHz) δ 7.75 (2H, m), 7.43 (2H, m), 6.54 (1H, s), 4.14 (1H, m), 3.70 (2H, m), 2.88 (3H, s), 2.86 (2H, m), 2.51 (3H, m), 2.08 (2H, m), 1.75 (4H, m), 1.51 (2H, m), 1.30 (6H, s), 1.21 (2H, m), 0.83 (3H, t, J=7.3 Hz). MS m/e 404 (M+H)⁺.

EXAMPLE 21

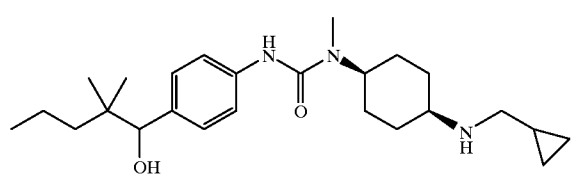

Reduction of Example 20A with NaBH₄ by the procedure of Example 18 afforded the title compound. ¹H NMR (CDCl₃, 400 MHz) δ 7.34 (2H, m), 7.20 (2H, m), 6.32 (1H, s), 4.40 (1H, s), 4.16 (1H, m), 2.93 (4H, s), 2.46 (2H, m), 1.88 (4H, m), 1.60 (2H, m), 1.49 (2H, m), 1.31 (4H, m), 0.99 (1H, m), 0.87 (6H, s), 0.79 (3H, m), 0.51 (2H, m), 0.15 (2H, m). MS m/e 416 (M+H)⁺.

Similarly prepared was:

21A

¹H NMR (CDCl₃, 400 MHz) δ 7.34 (2H, m), 7.21 (2H, m), 6.31 (1H, s), 4.41 (1H, s), 4.18 (1H, m), 2.93 (3H, s), 2.78 (1H, m), 2.43 (3H, s), 1.87 (4H, m), 1.62 (2H, m), 1.49 (2H, m), 1.31 (4H, m), 0.87 (6H, s), 0.79 (3H, m). MS m/e 376 (M+H)⁺.

EXAMPLE 22

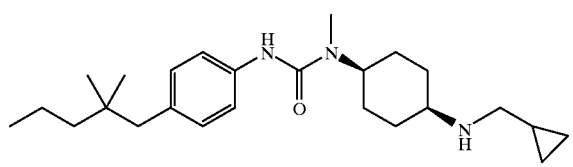

Reduction of Example 20 with Et₃SiH/TFA by the procedure of Example 19 afforded the title compound. ¹H NMR (CDCl₃, 400 MHz) δ 7.28 (2H, m), 7.10 (2H, m), 6.26 (1H, s), 4.16 (1H, m), 2.93 (3H, s), 2.89 (1H, m), 2.47 (2H, m), 2.43 (2H, s), 1.87 (4H, m), 1.60 (2H, m), 1.48 (2H, m), 1.31 (2H, m), 1.16 (2H, m), 0.99 (1H, m), 0.88 (3H, t, J=7.3 Hz), 0.81 (6H, s), 0.50 (2H, m), 0.15 (2H, m). MS m/e 400 (M+H)⁺.

Similarly, the following compound was prepared:

22A

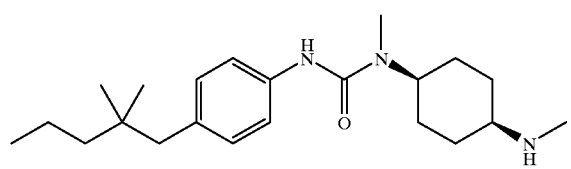

¹H NMR (CDC₃, 400 MHz) δ 7.27 (2H, m), 7.01 (2H, m), 6.26 (1H, s), 4.18 (1H, m), 2.92 (3H, s), 2.77 (1H, m), 2.43

(5H, s), 1.88 (4H, m), 1.66 (2H, m), 1.50 (2H, t), 1.30 (2H, m), 1.11 (2H, m), 0.88 (3H, s), 0.81 (6H, s). MS m/e 360 (M+H)$^+$.

EXAMPLE 23

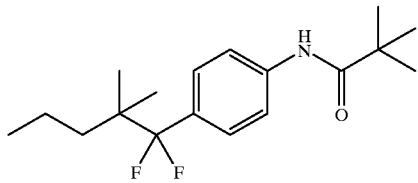

Step 1:

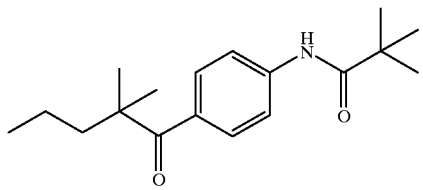

Using the procedure of Example 1, reaction of Preparation 8, trimethyl acetyl chloride and pyridine gave the product. $^1$H NMR (CDCl$_3$, 400 MHz) δ 7.76 (d, 2H, J=8.8 Hz, ArH), 7.57 (d, 2H, J=8.4 Hz, ArH), 7.41 (s, 1H, NH), 1.75 (m, 2H, CH$_3$CH$_2$CH$_2$), 1.32 (s, 9H, (CH$_3$)$_3$C), 1.30 (s, 6H, (CH$_2$)$_2$C), 1.26 (m, 2H, CH$_2$CH$_3$), 0.84 (t, 3H, J=7.2 Hz, CH$_3$CH$_2$). MS m/e 290 (M+H)$^+$.

Step 2: To a solution of the product of Step 1 (100 mg, 0.346 mmol) in dry CH$_2$Cl$_2$ (1.0 ml) was added (diethylamino)sulfur trifluoride (557 mg, 3.46 mmol). The reaction mixture was heated at 80° C. overnight, then allowed to cool to RT. The crude mixture was subjected to plc (1:6 EtOAc/hexanes) to give the product (25.0 mg, 23%) as a colorless oil. $^1$H NMR (CDCl$_3$, 400 MHz) δ 7.37 (m, 2H, ArH), 7.26 (m, 2H, ArH), 1.32 (m, 13H, (CH$_3$)$_3$C & CH$_3$CH$_2$CH$_2$), 0.98 (s, 6H, (CH$_3$)$_2$C), 0.87 (m, 3H, CH$_3$CH$_2$). MS m/e 312 (M+H)$^+$.

What is claimed is:

1. A compound having the structural formula

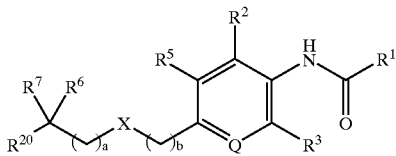

or a pharmaceutically acceptable salt thereof, wherein
a and b are independently 0, 1 or 2, provided that the sum of a and b is 0 to 3;
Q is

X is —S—, —C(O)—, —CH(OR$^8$)— or —C(R$^{23}$)$_2$—;
R$^1$ is —N(C$_1$–C$_6$ alkyl)(R$^{12}$);
R$^2$, R$^3$, R$^4$ and R$^5$ are independently selected from the group consisting of H, C$_1$–C$_5$ straight or branched alkyl, (C$_3$–C$_{12}$)cycloalkyl, R$^{14}$—(C$_3$–C$_{12}$)cycloalkyl, halogen, —OR$^8$, —N(R$^8$)$_2$, —CO$_2$R$^8$ and CF$_3$;

R$^6$ and R$^7$ are independently selected from the group consisting of H, (C$_1$–C$_9$)alkyl, (C$_1$–C$_9$)alkenyl, hydroxy-(C$_1$–C$_9$)alkyl, amino-(C$_1$–C$_9$)-alkyl, (C$_1$–C$_9$) alkoxy-(C$_1$–C$_9$)alkyl, (C$_3$–C$_{12}$)cycloalkyl and (C$_3$–C$_{12}$)-cycloalkyl-(C$_1$–C$_6$)alkyl, or R$^6$ and R$^7$, together with the carbon to which they are attached, form a 3, 4, 5, 6 or 7-membered carbocyclic ring, or a 4, 5, 6 or 7-membered heterocyclic ring, wherein 1, 2 or 3 ring members are independently selected from the group consisting of O, S and N;
R$^8$ is independently selected from the group consisting of H, (C$_1$–C$_6$)alkyl, (C$_3$–C$_{12}$)cycloalkyl, R$^{15}$-aryl and R$^{24}$-heteroaryl;
R$^9$ is (C$_1$–C$_6$)alkyl, (C$_3$–C$_{12}$)cycloalkyl, R$^{15}$-aryl or R$^{24}$-heteroaryl;
R$^{12}$ is

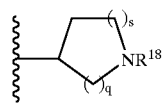

wherein q is 1 or 2, and s is 0, 1 or 2;
R$^{13}$ is 1 to 3 substituents independently selected from the group consisting of hydrogen, (C$_1$–C$_6$)alkyl, halogen, (C$_1$–C$_6$)alkoxy and CF$_3$;
R$^{14}$ is 1 to 3 substituents independently selected from the group consisting of (C$_1$–C$_6$)alkyl, benzyl, R$^{13}$-aryl and R$^{13}$-heteroaryl;
R$^{15}$ is 1 to 3 substituents independently selected from the group consisting of hydrogen, (C$_1$–C$_6$)alkyl, halo, polyhalo(C$_1$–C$_6$)alkyl, R$^{17}$O—, —N(R$^{17}$)$_2$, —S(R$^{17}$), R$^{17}$O—(C$_1$–C$_6$)alkyl, (R$^{17}$)$_2$N—(C$_1$–C$_6$)alkyl, formyl, —C(O)R$^{17}$, —COOR$^{17}$, —CON(R$^{17}$)$_2$, —OC(O)N (R$^{17}$)$_2$, —N(R$^{17}$)C(O)N(R$^{17}$)$_2$, —NR$^{17}$C(O)R$^{17}$, —NR$^{17}$C(O)OR$^{14}$, R$^{17}$S(O)—, R$^{17}$SO$_2$—, R$^{17}$SO$_2$NR$^{17}$— and tri(C$_1$–C$_6$)-alkylsilyl;
R$^{17}$ is independently selected from the group consisting of H, (C$_1$–C$_6$)alkyl, (C$_3$–C$_{12}$)cycloalkyl, (C$_3$–C$_{12}$) cycloalkyl(C$_1$–C$_6$)alkyl, R$^{13}$-aryl and R$^{13}$-heteroaryl;
R$^{18}$ is independently selected from the group consisting of H, (C$_1$–C$_6$)alkyl, (C$_3$–C$_{12}$)cycloalkyl, (C$_3$–C$_{12}$) cycloalkyl-(C$_1$–C$_6$)alkyl, R$^{15}$-aryl, R$^{24}$-heteroaryl, —CO$_2$R$^9$, —C(O)N(R$^8$)$_2$, —COR$^8$ and —SO$_2$R$^9$;
R$^{20}$ is (C$_1$–C$_6$)alkyl, (C$_3$–C$_{12}$)cycloalkyl, (C$_3$–C$_{12}$) cycloalkyl-(C$_1$–C$_6$)alkyl, hydroxy(C$_1$–C$_6$)alkyl, oxo (C$_1$–C$_6$)alkyl or polyhalo(C$_1$–C$_6$)alkyl;
R$^{23}$ is independently selected from the group consisting of H, halogen, (C$_1$–C$_6$)alkyl, (C$_3$–C$_{12}$)cycloalkyl, R$^{15}$-aryl, and R$^{24}$-heteroaryl; and
R$^{24}$ is 1 to 2 substituents independently selected from the group consisting of hydrogen, (C$_1$–C$_6$)alkyl, halo, polyhalo(C$_1$–C$_6$)alkyl, R$^{17}$O—, —N(R$^{17}$)$_2$, —S(R$^{17}$), R$^{17}$O—(C$_1$–C$_6$)alkyl, (R$^{17}$)$_2$N—(C$_1$–C$_6$)alkyl, formyl, —C(O)R$^{17}$, —COOR$^{17}$, —CON(R$^{17}$)$_2$, —OC(O)N (R$^{17}$)$_2$, —N(R$^{17}$)C(O)N(R$^{17}$)$_2$, —NR$^{17}$C(O)R$^{17}$, —NR$^{17}$C(O)OR$^{14}$, R$^{17}$S(O)—, R$^{17}$SO$_2$—, R$^{17}$SO$_2$NR$^{17}$— and tri(C$_1$–C$_6$)-alkylsilyl.

2. A compound of claim 1 wherein R$^3$ and R$^4$ are each H; and R$^2$ and R$^5$ are independently selected from the group consisting of hydrogen and halogen.

3. A compound of claim 1 wherein X is —S—; —C(O)—; —CH(OR$^8$)— or —C(R$^{23}$)$_2$—.

4. A compound of claim 3 wherein X is —C(R$^{23}$)$_2$— and R$^{23}$ is hydrogen.

5. A compound of claim 1 wherein a is 1 or 2 and b is 0.

6. A compound of claim 1 wherein $R^6$ and $R^7$ are each $(C_1-C_6)$alkyl, or $R^6$ and $R^7$, together with the carbon to which they are attached, form a $C_3-C_6$ carbocyclic ring.

7. A compound of claim 1 selected from the group consisting of those having the structural formula

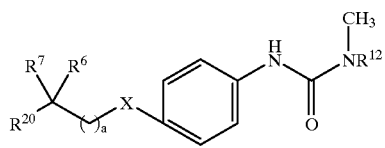

wherein $R^{20}$, $R^6$, $R^7$, a, X, and $R^{12}$ are as defined in the following table:

-continued
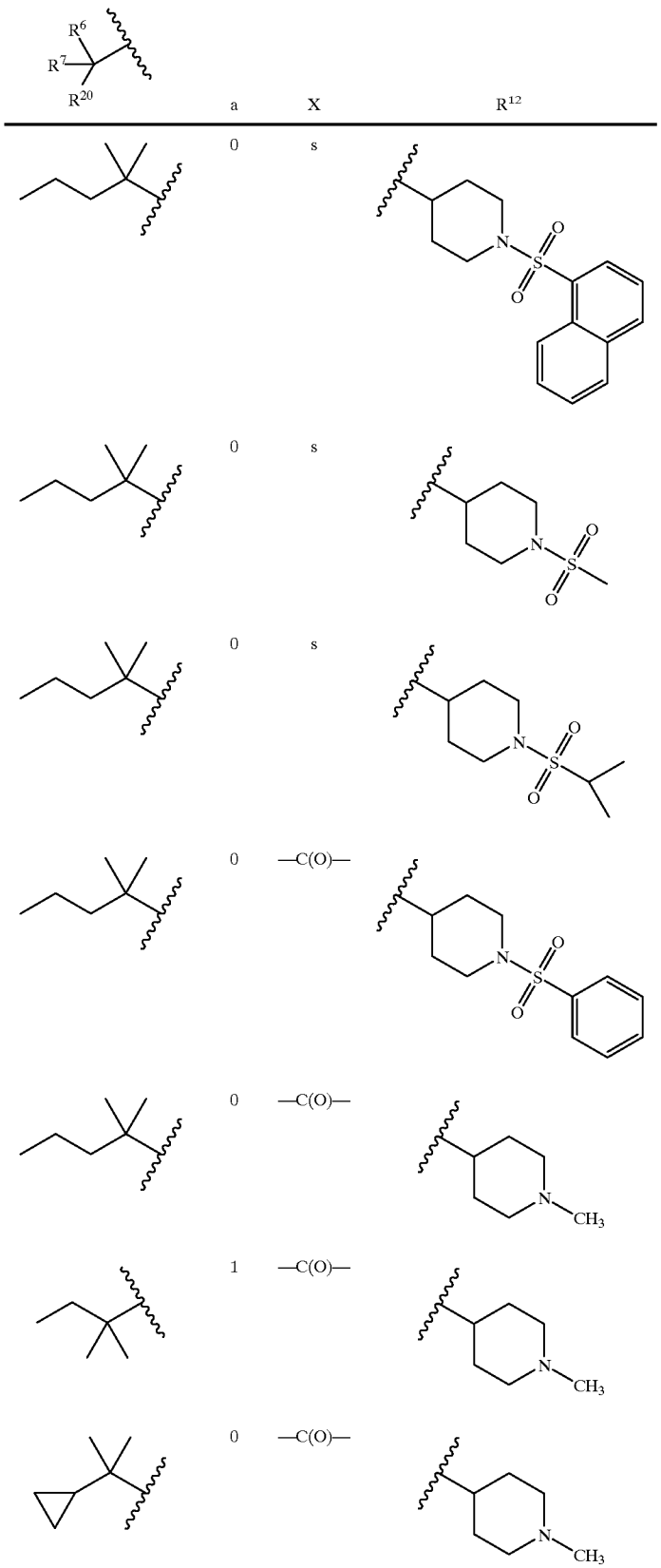

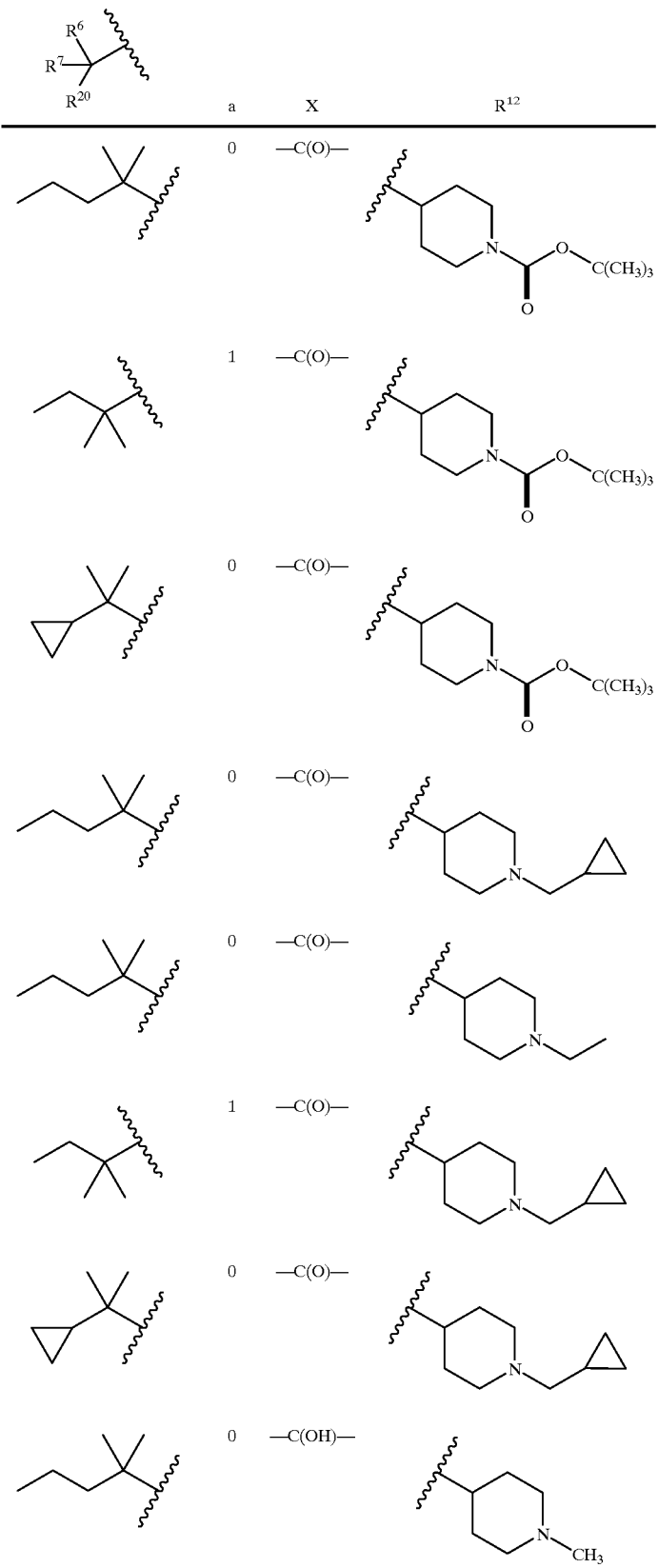

-continued
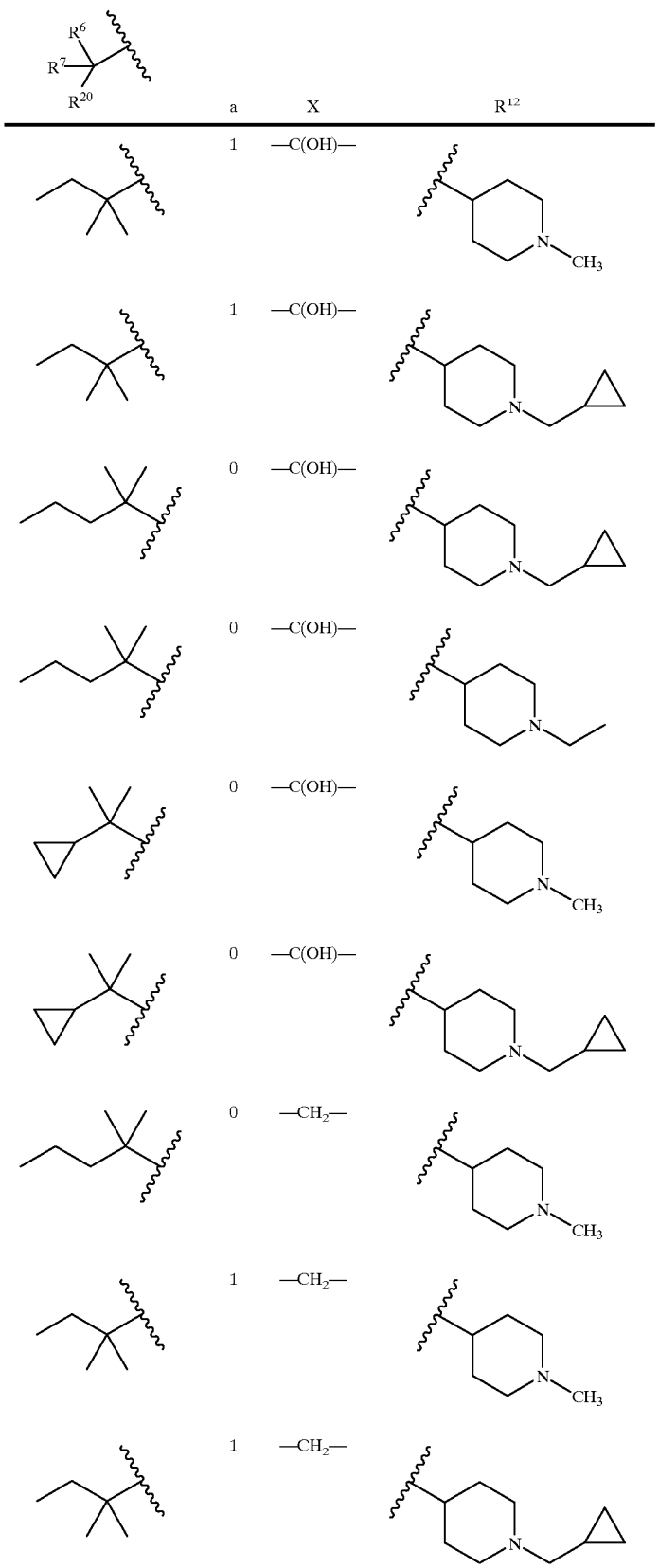

-continued
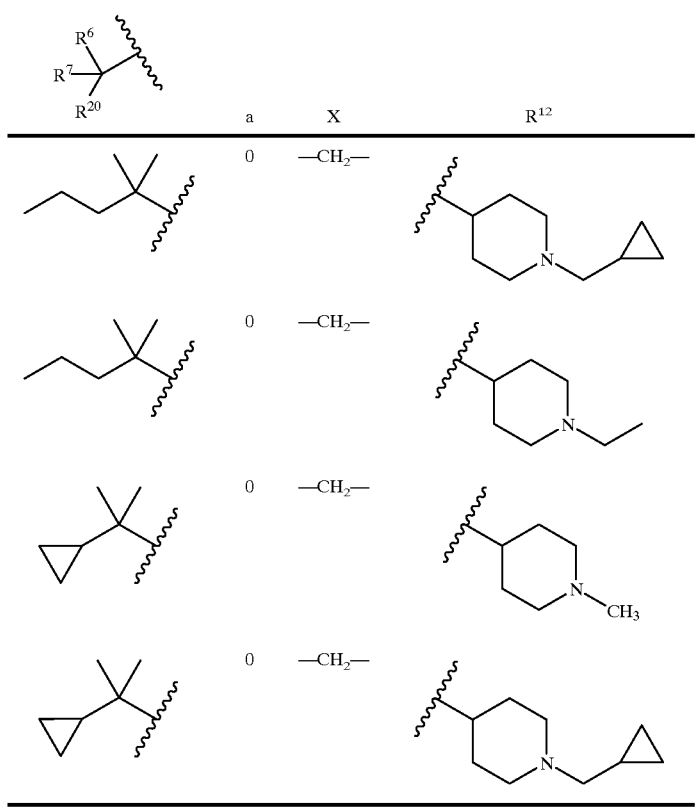
8. A pharmaceutical composition comprising a compound as defined in claim 1 in combination with a pharmaceutically acceptable carrier.
9. A method of treating an eating disorder or diabetes comprising administering an effective amount of a compound of claim 1 to a mammal in need of such treatment.
* * * * *